US012576256B2

(12) United States Patent
Bonaldo et al.

(10) Patent No.: US 12,576,256 B2
(45) Date of Patent: Mar. 17, 2026

(54) MEDICAL LUER CONNECTOR

(71) Applicant: Halkey-Roberts Corporation, St. Petersburg, FL (US)

(72) Inventors: Jean M. Bonaldo, Upland, CA (US); Pavel T. Miller, St. Petersburg, FL (US)

(73) Assignee: HALKEY-ROBERTS CORPORATION, St. Petersburg, FL (US)

( * ) Notice: Subject to any disclaimer, the term of this patent is extended or adjusted under 35 U.S.C. 154(b) by 0 days.

(21) Appl. No.: 14/886,081

(22) Filed: Oct. 18, 2015

(65) Prior Publication Data

US 2017/0106181 A1     Apr. 20, 2017

(51) Int. Cl.
*A61M 39/10* (2006.01)
*A61M 39/24* (2006.01)
*A61M 39/26* (2006.01)

(52) U.S. Cl.
CPC ........ *A61M 39/10* (2013.01); *A61M 39/1011* (2013.01); *A61M 39/24* (2013.01); *A61M 39/26* (2013.01); *A61M 2039/1033* (2013.01); *A61M 2039/1072* (2013.01); *A61M 2039/2426* (2013.01); *A61M 2039/267* (2013.01); *A61M 2205/583* (2013.01); *A61M 2205/584* (2013.01); *A61M 2205/6063* (2013.01)

(58) Field of Classification Search
CPC .............. A61M 39/10; A61M 39/1011; A61M 2039/1033; A61M 2039/1072; A61M 2039/267; A61M 39/24; A61M 39/26; A61M 2039/2426; A61M 2039/2433; A61M 2205/6063; A61M 2205/583; A61M 2205/584; A61M 2039/1027; A61M 2039/1038; A61M 2039/1077; A61M 2039/1083; A61M 2039/1088; A61M 2039/2486; A61M 2039/261; A61M 2039/263; A61M 2039/268; A61M 39/105; A61M 39/1055; A61M 39/22; A61M 39/045
See application file for complete search history.

(56) References Cited

U.S. PATENT DOCUMENTS

| | | | | |
|---|---|---|---|---|
| 5,273,533 | A | 12/1993 | Bonaldo | |
| 5,306,243 | A * | 4/1994 | Bonaldo | A61M 39/04 |
| | | | | 604/167.03 |
| 5,947,954 | A | 9/1999 | Bonaldo | |
| 6,126,359 | A | 10/2000 | Dittrich et al. | |
| 7,118,560 | B2 | 10/2006 | Bonaldo | |

(Continued)

FOREIGN PATENT DOCUMENTS

| | | |
|---|---|---|
| CA | 3002146 A1 | 4/2017 |
| CN | 201000543 Y | 1/2008 |
| WO | 2015074044 A1 | 5/2015 |

*Primary Examiner* — Kevin C Sirmons
*Assistant Examiner* — Alexandra Lalonde
(74) *Attorney, Agent, or Firm* — Calfee, Halter & Griswold LLP

(57) ABSTRACT

A Luer medical connector having a male Luer body for connection with a female Luer assembly which includes a female Luer body, a fluid channel insert within the female Luer body, an elastomeric seal between the female Luer body and the male Luer body, and an elastomeric stopper at a proximal end of the female Luer body.

20 Claims, 66 Drawing Sheets

(56) References Cited

U.S. PATENT DOCUMENTS

| | | | | |
|---|---|---|---|---|
| 8,105,314 | B2 * | 1/2012 | Fangrow, Jr. ......... | A61M 39/10 |
| | | | | 251/149.1 |
| 2003/0116162 | A1 | 6/2003 | Madsen et al. | |
| 2004/0171993 | A1 | 9/2004 | Bonaldo | |
| 2004/0172006 | A1 * | 9/2004 | Bonaldo ............... | A61M 39/26 |
| | | | | 604/523 |
| 2005/0107770 | A1 * | 5/2005 | Schweikert .......... | A61M 39/10 |
| | | | | 604/533 |
| 2009/0281632 | A1 | 11/2009 | Naidu | |
| 2010/0063482 | A1 * | 3/2010 | Mansour ............... | A61M 39/22 |
| | | | | 604/539 |
| 2011/0282302 | A1 * | 11/2011 | Lopez ................... | A61M 39/10 |
| | | | | 604/247 |

* cited by examiner

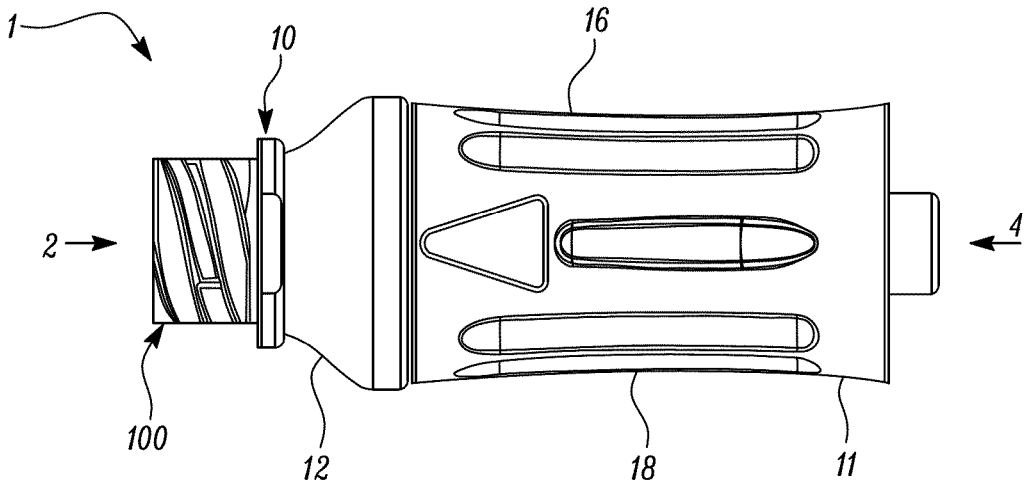
FIG. 1B/C

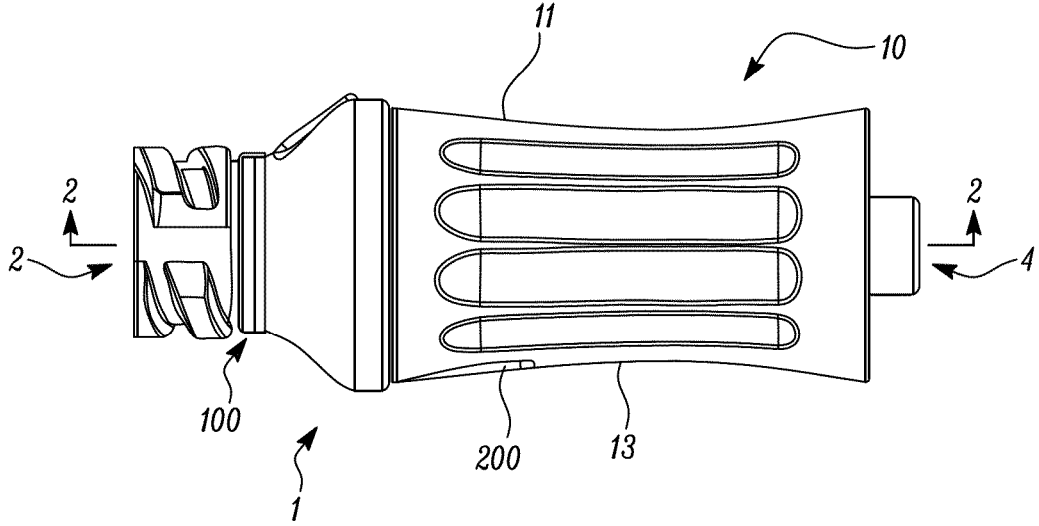
FIG. 2B/C

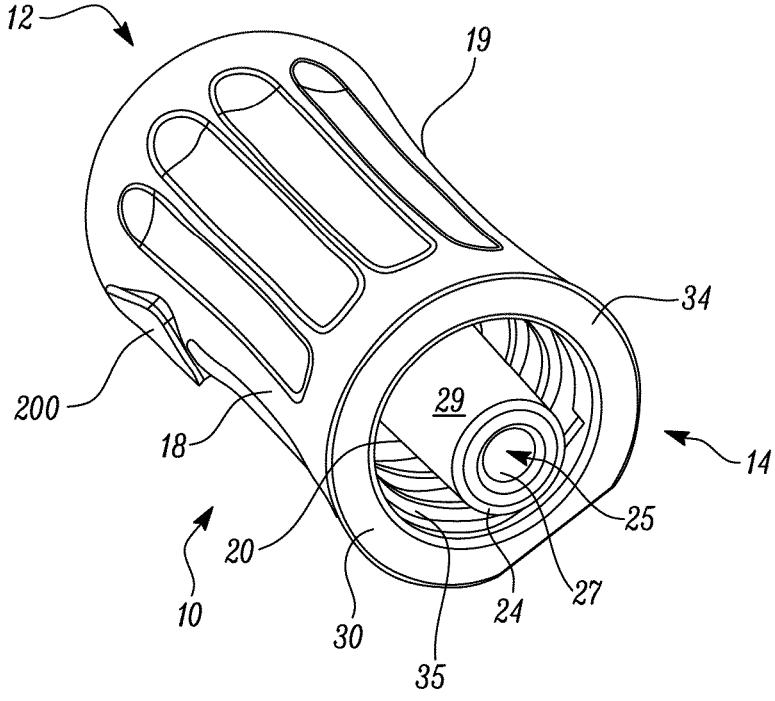
FIG. 4B/C

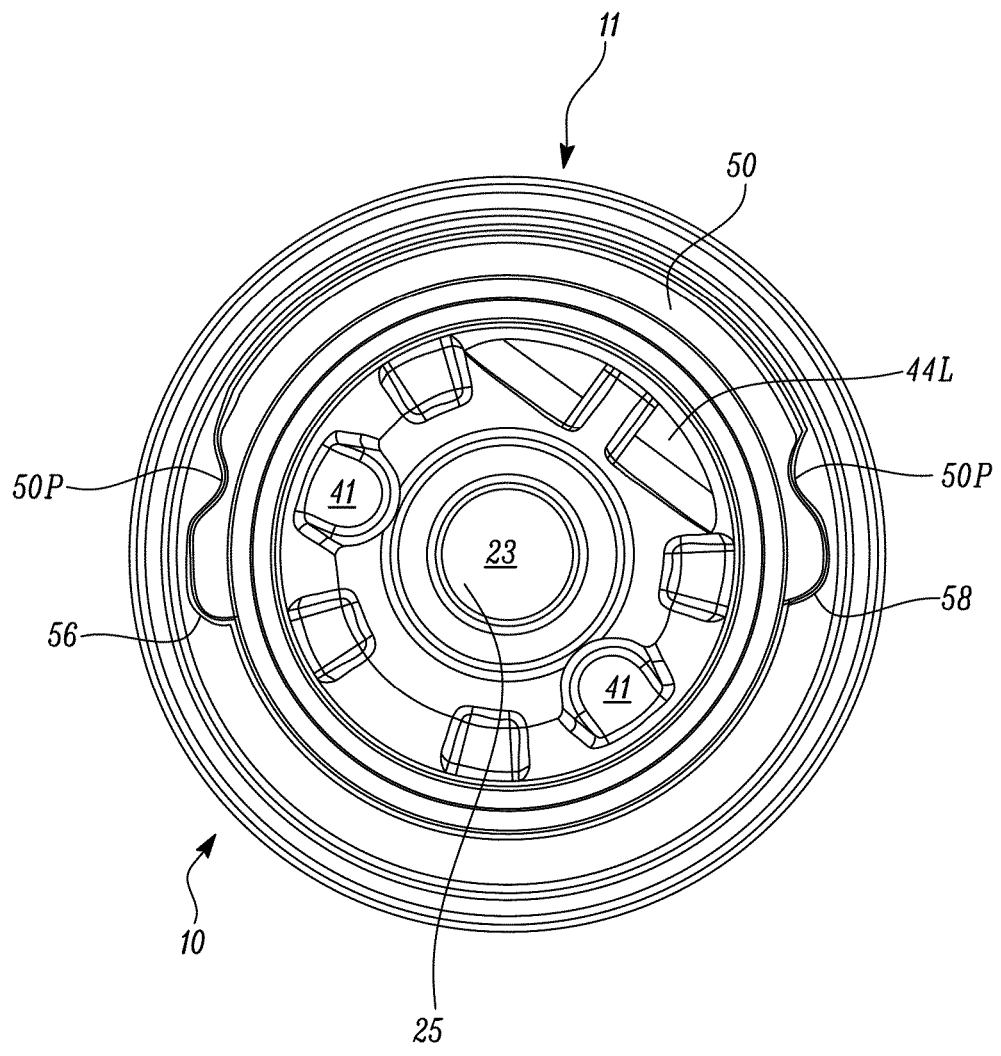
FIG. 5B/C

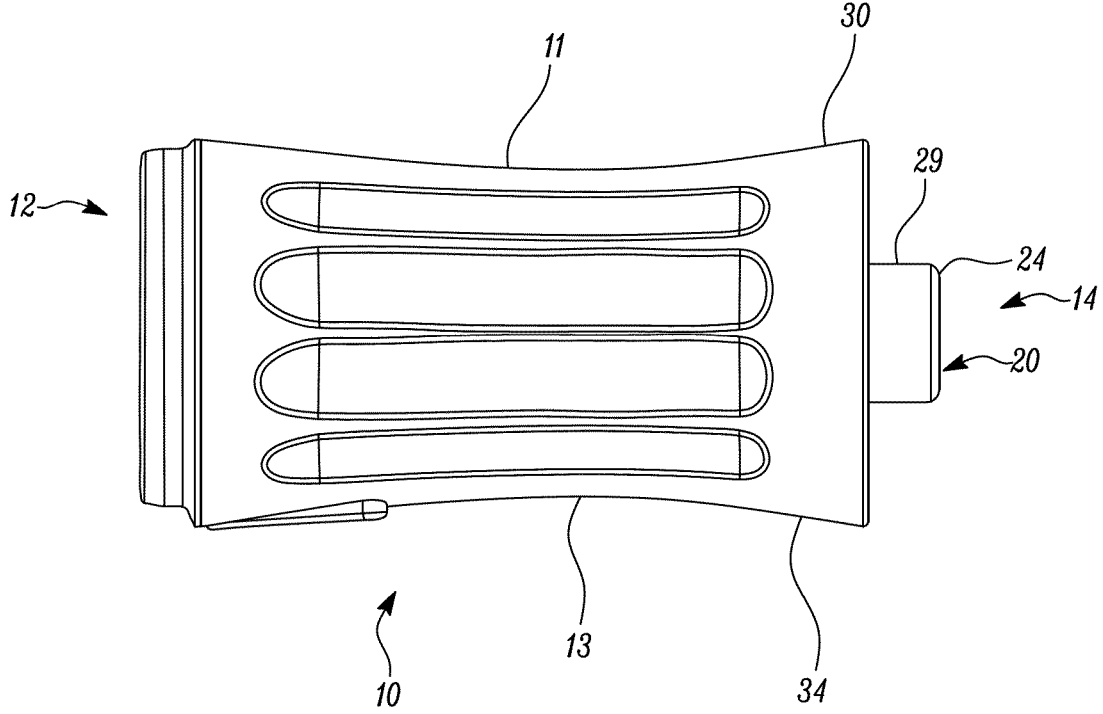
FIG. 6B/C

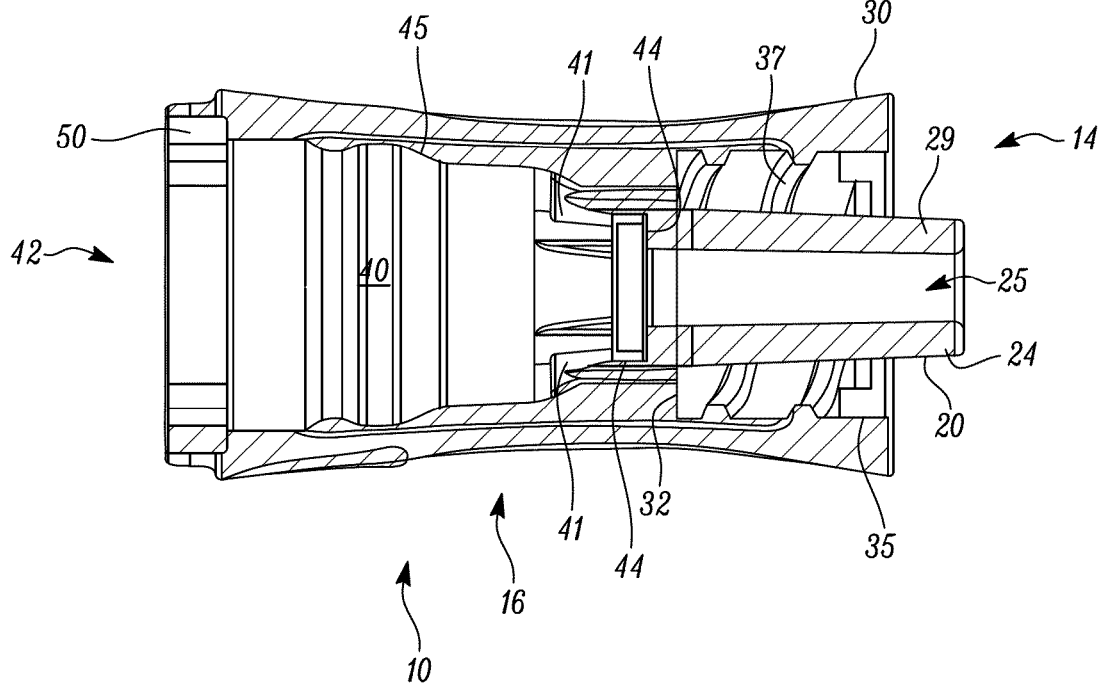
FIG. 7B/C

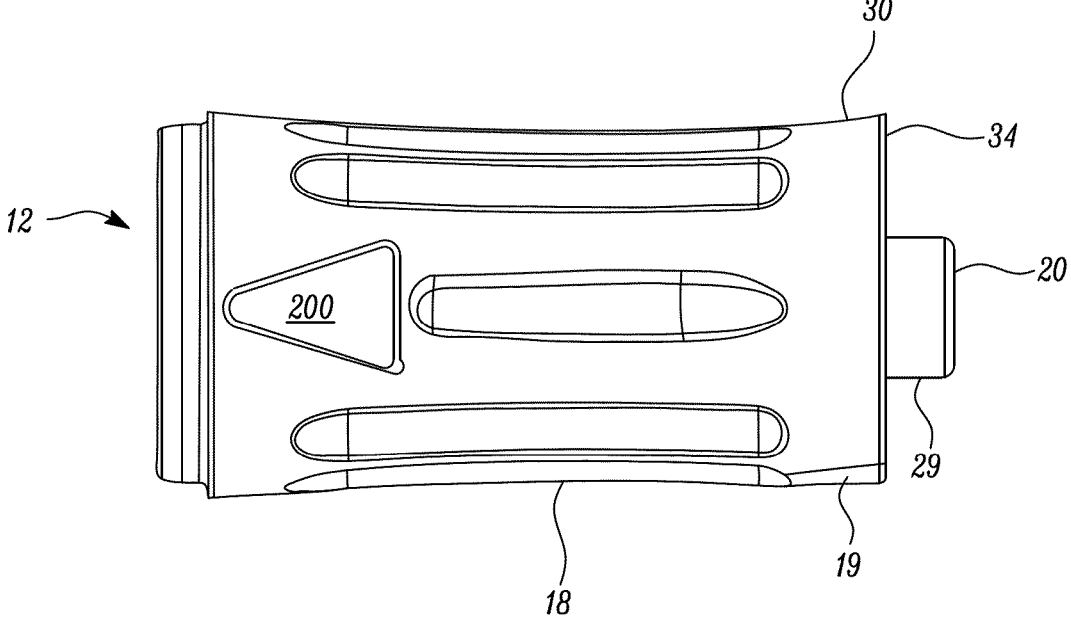
FIG. 8B/C

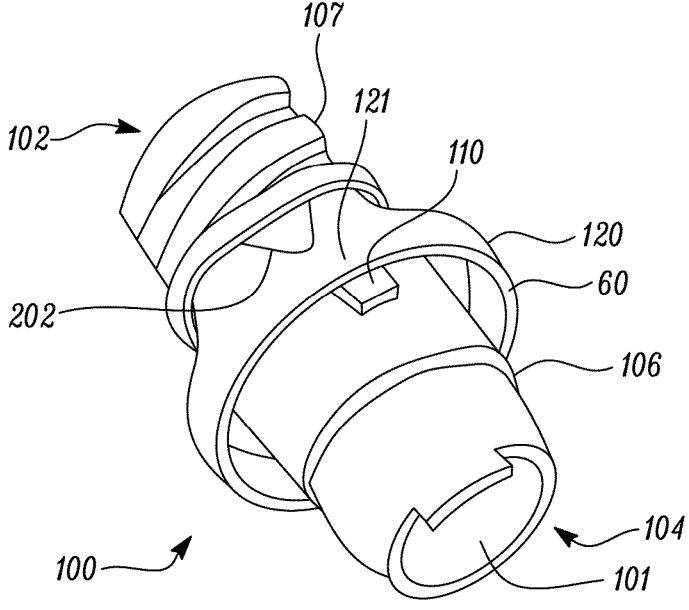
FIG. 11B/C

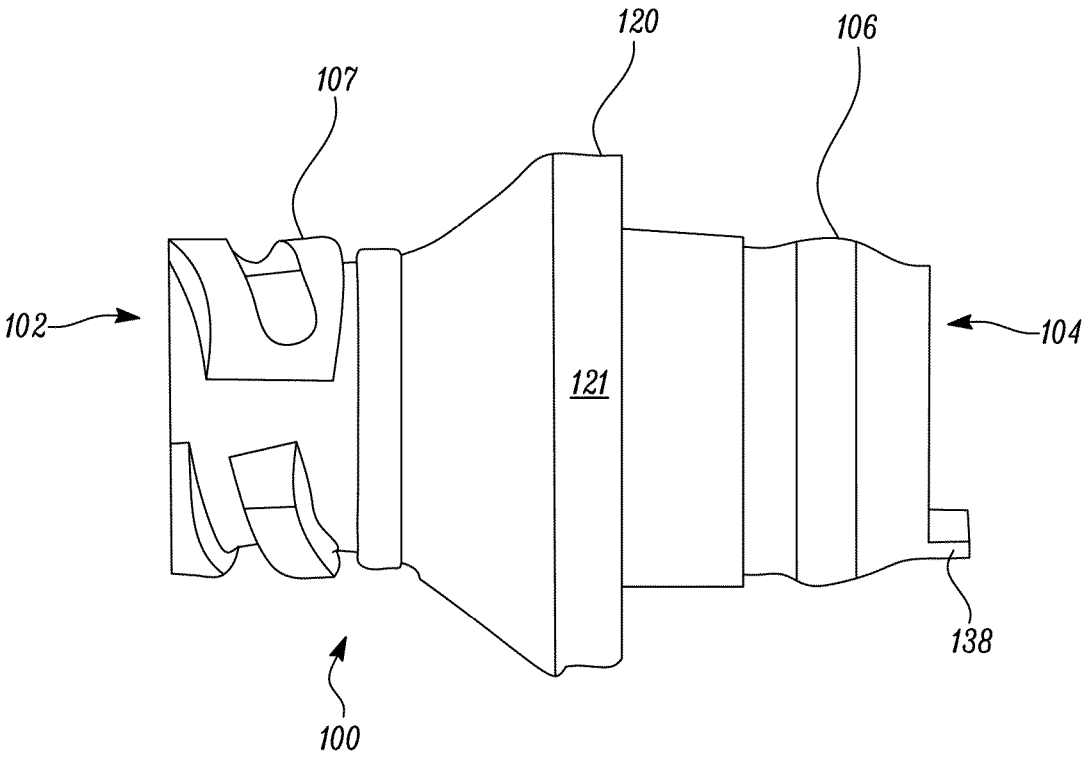
FIG. 12B/C

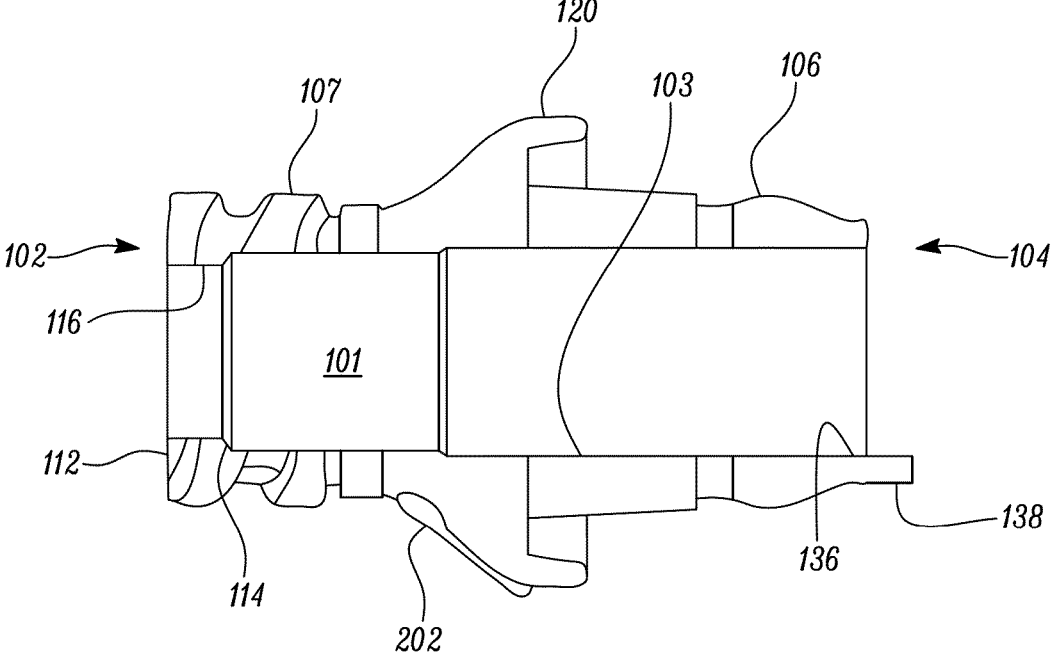
FIG. 13B/C

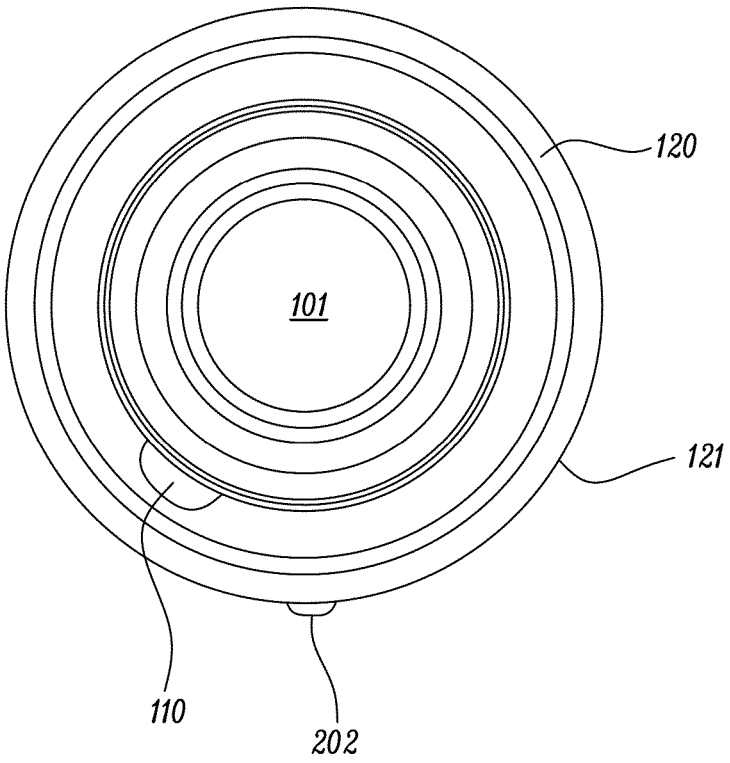
FIG. 14B/C

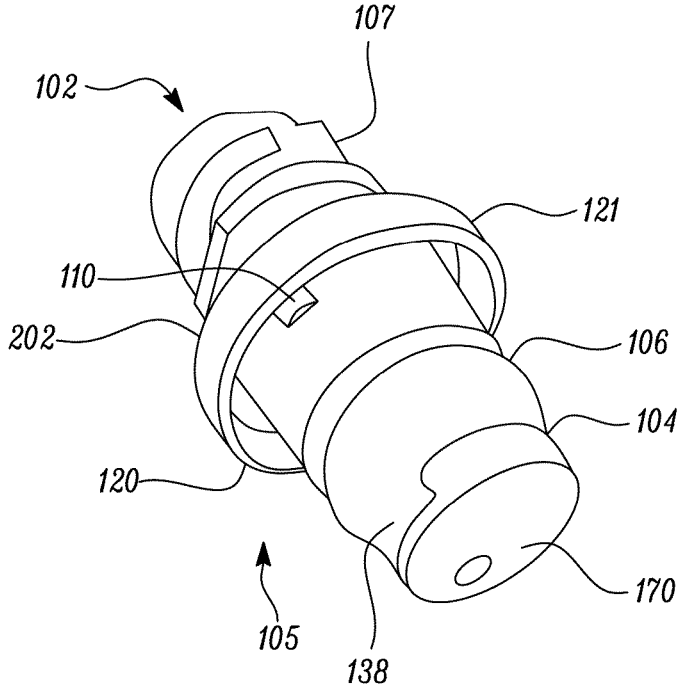
FIG. 15B/C

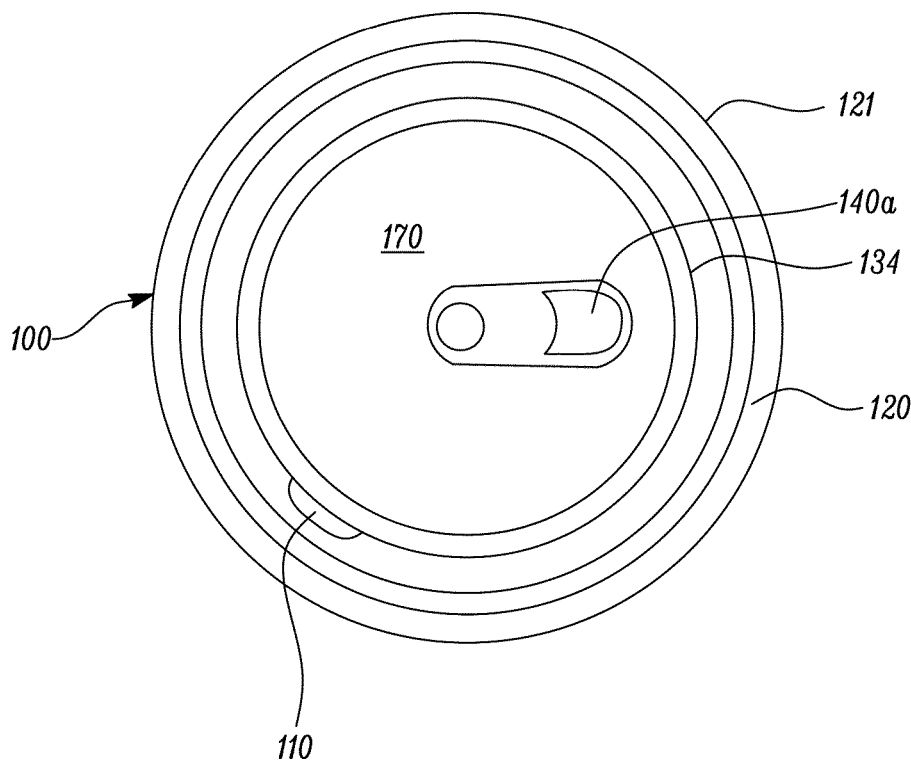
FIG. 16B/C

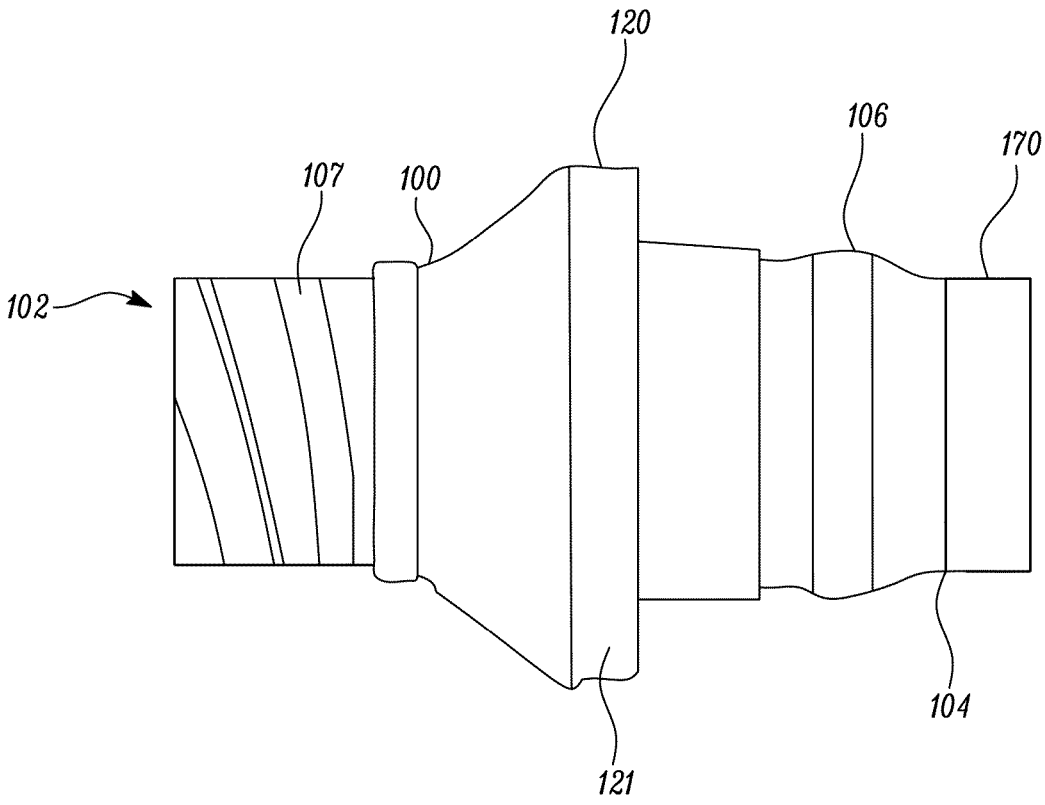
FIG. 18B/C

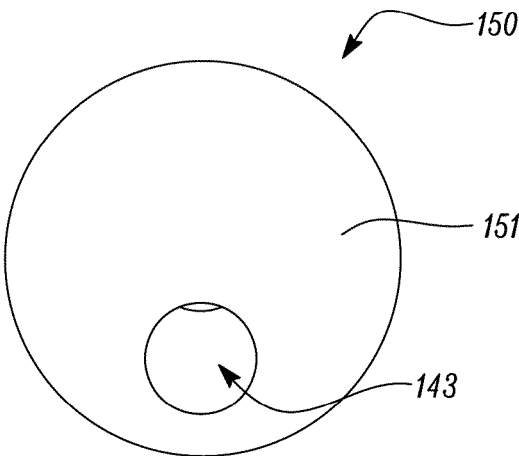
FIG. 24A/B

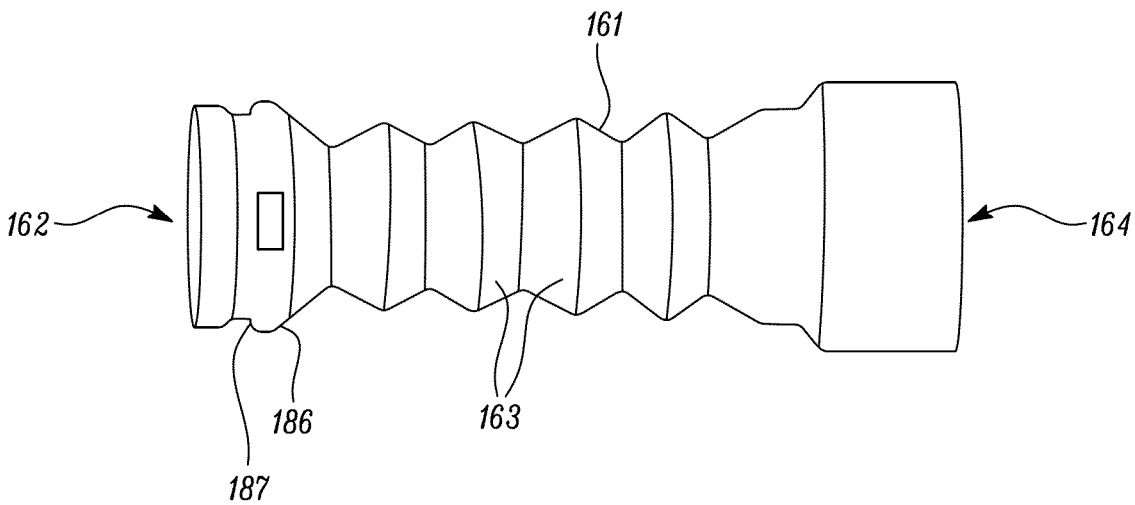
FIG. 26B/C

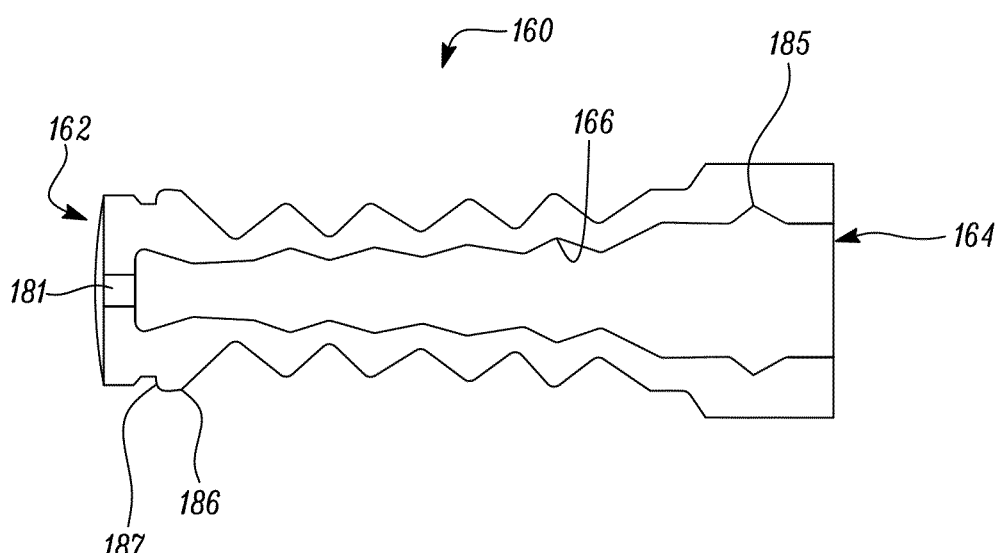
FIG. 27B/C

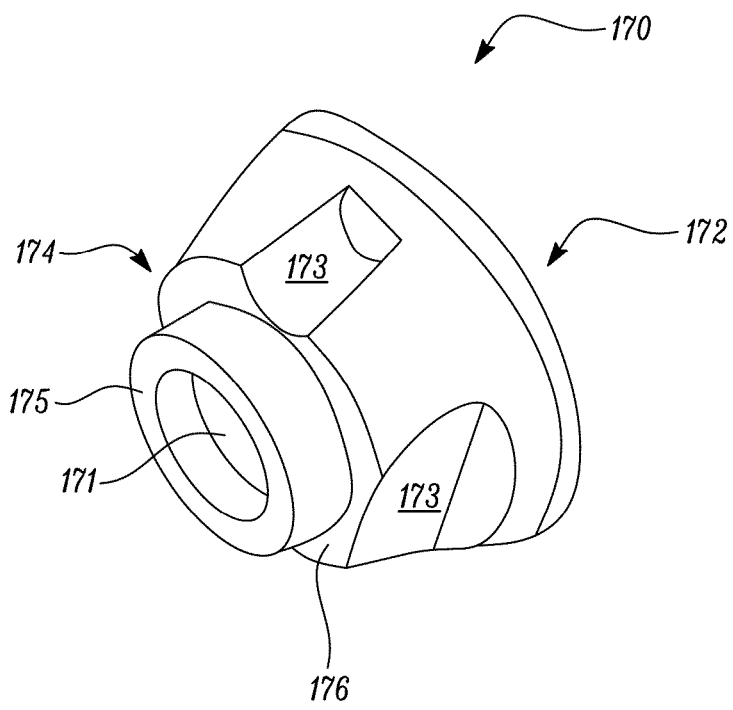
FIG. 28 B/C

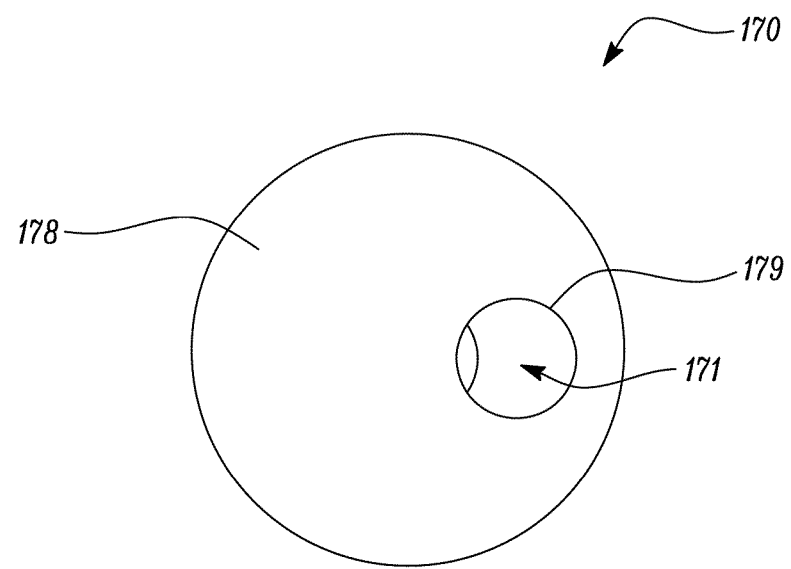
FIG. 29A/B/C

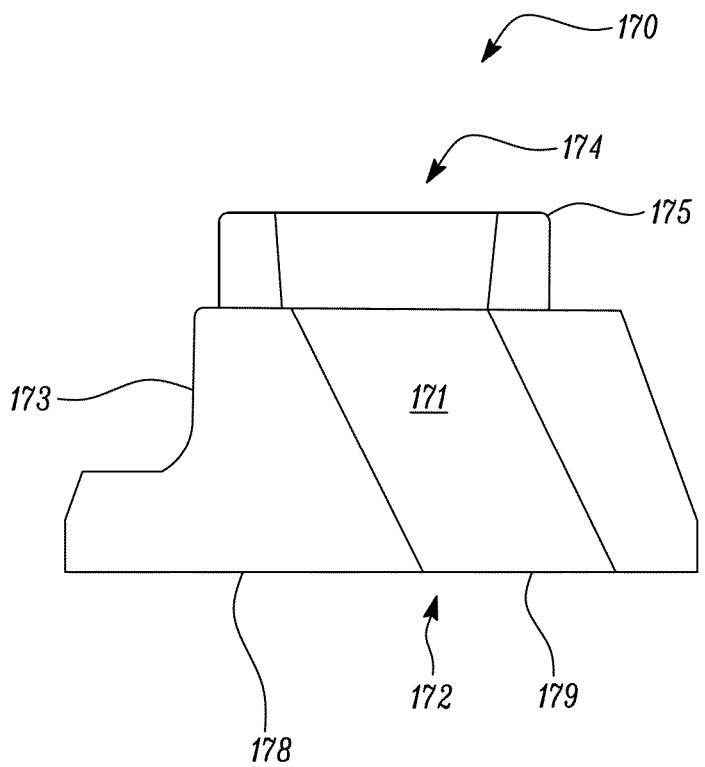
FIG. 32 B/C

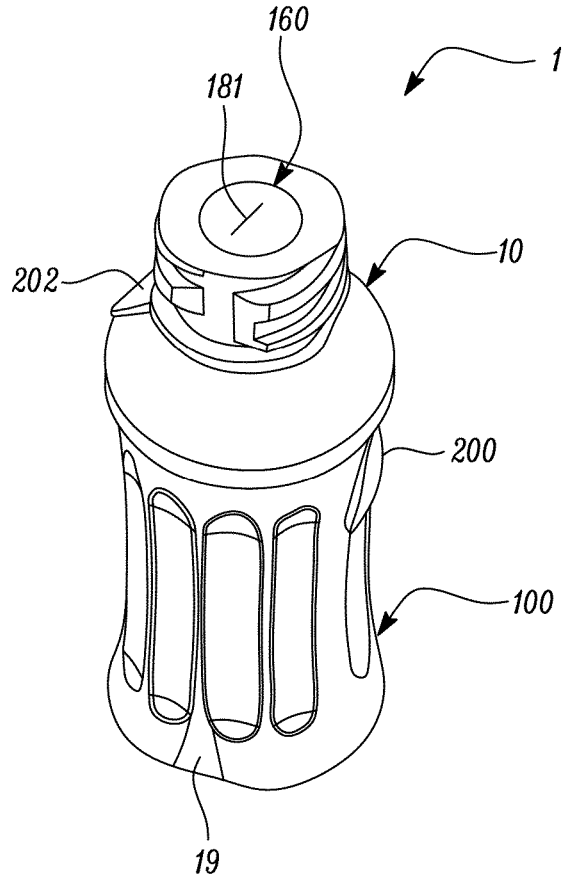
FIG. 33 B/C (CLOSED)

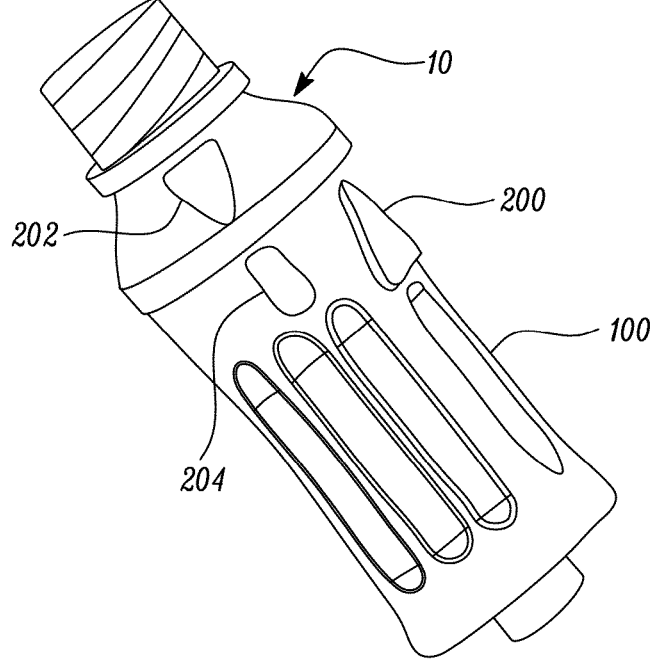
FIG. 33D (CLOSED)

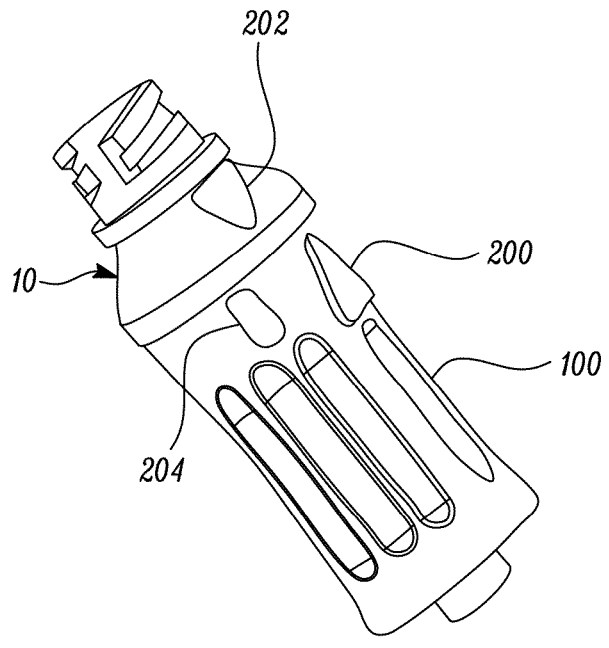
FIG. 33D (OPEN)

MEDICAL LUER CONNECTOR

BACKGROUND OF THE INVENTION

Field of the Invention

This invention relates to Luer connectors.

Description of the Background Art

Presently, Luer connectors are widely used to connect medical devices involved in transferring medical fluids, and can be found for example on syringes, catheters, and connectors for IV tubing. Luer connectors comprise interlocking male (outer) and female (inner) portions which are slightly tapered so as to connect via a pressure or interference fit in a fluid-tight manner. When the male and female portions are joined with a threaded connection, the connection is referred to as a Luer lock, which opens and closes by twisting. A non-threaded Luer connection is generally referred to as a Luer plug or Luer slip.

Male and female Luer connector portions cooperate to communicatively couple separate devices or pieces of medical tubing and form a single flow pathway. For example, one length of tubing can be attached to a male Luer connector and another length of tubing can be attached to a female Luer connector. The separate lengths of tubing can then be placed into fluid communication by coupling the male Luer connector portion and the female Luer connector portion.

In some circumstances, Luer connectors may be connected to and disconnected from flow lines on at least a daily basis. Repeated usage of a Luer connector, however, may cause the connector to leak or become contaminated with particulate material, such as particles that detach from the septum of the connector and/or cotton fibers from swabs used to clean the connectors. Connectors must remain leak free and reliably avoid introduction of contaminants.

A variety of Luer connections are known. U.S. Pat. Nos. 5,273,533 and 5,306,243 to Bonaldo, for example, disclose a medical connector having an elastomeric element in the form of a septum or fluid barrier disposed in a two part plastic housing. The septum is pierced by a pointed cannula in the connector when making the connection to the fluid flow line. U.S. Pat. No. 5,947,954 to Bonaldo discloses a needleless connector which includes attached relatively rotatable male and female Luer connector parts with an eccentrically positioned flow passageway at the inner end of the female Luer connector. Further needleless Luer connectors include that of U.S. Pat. No. 7,118,560, also to Bonaldo.

Therefore, it is an object of this invention to provide an improvement which overcomes the aforementioned inadequacies of the prior art devices and provides an improvement which is a significant contribution to the advancement of the medical Luer connector art.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

There remains a need to provide a further improved medical connector which includes a female Luer end having an elastomeric stopper which achieves zero displacement and thereby reduces the likelihood of contaminant entry to the fluid flow path of the connector.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings. The drawings suffixed with the letter "A" refer to the first embodiment of the parent application. The drawings suffixed with the letter "B" refer to the second embodiment employing an extended blunt tube channel insert. The drawings suffixed with the letter "C" refer to a third embodiment employing a spike tube channel insert. The drawings suffixed with the letter "D" refer to a fourth embodiment employing "open" and "closed" indicators positioned at 120 degrees so they are visible at any angle. Combined suffixes such as B/C to the drawing number mean that the drawing is applicable to both the B or second embodiment and the C or third embodiment. The lack of a suffix to a drawing number (e.g.

FIGS. 3 A, B & C are each a sectional view of the present medical Luer connector assembly along line 2-2 of FIG. 2.

FIGS. 29 A/B/ C are each a rear elevation view of the seal of the present Luer connector.

FIGS. 33 B/C (CLOSED), D (OPEN) & D (CLOSED) are each a perspective view showing the indicators for indicating the "ON" and "OFF" positions.

Similar reference characters refer to similar parts throughout the several views of the drawings.

DETAILED DESCRIPTION OF THE PREFERRED EMBODIMENT

Definitions

Figure 1A:
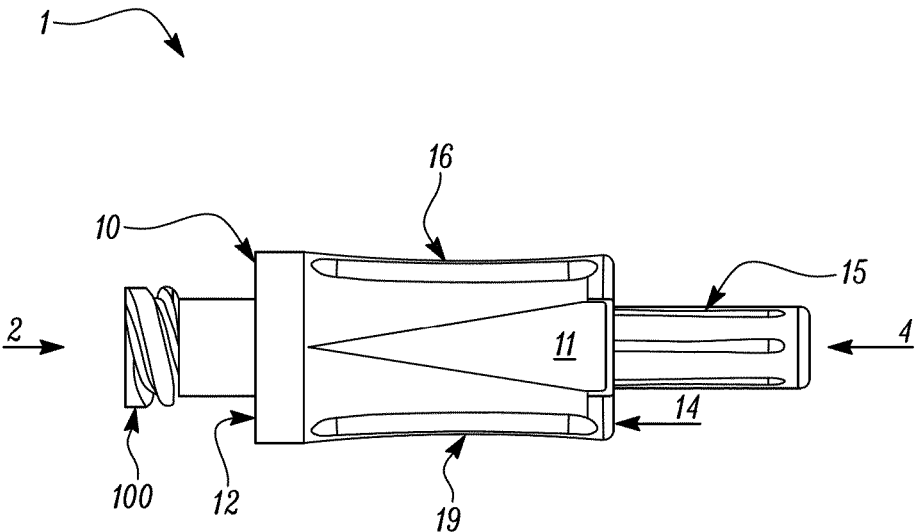
FIGS. 1 A & B/C are a top plan view of the present medical Luer connector assembly.
Figure 2A:
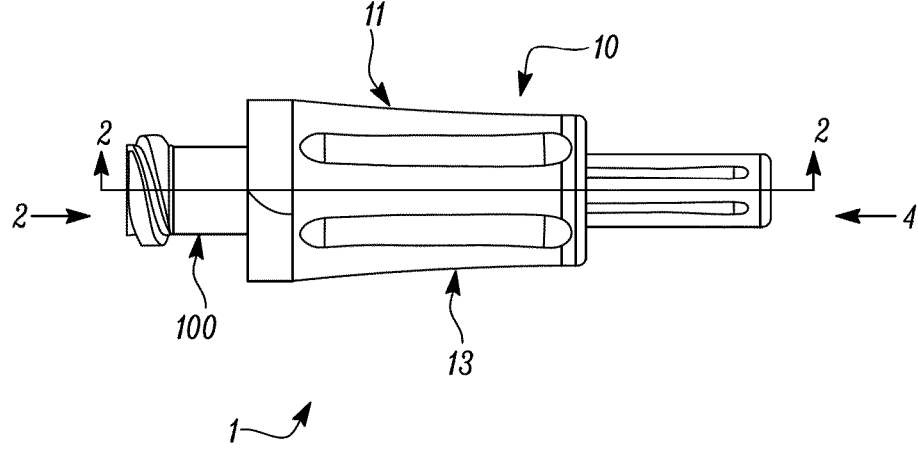
FIGS. 2 A & B/C are each a side elevation view of the present medical Luer connector assembly.

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

"Annular" refers a component or portion thereof forming a ring, and is inclusive of a partial or complete ring-shaped structure, for example, a tubular structure, a "c-shape," a "u-shape," or an "o-shape."

"Cam and groove" fitting or coupling refers to a connection between two components in which a projection or "cam" on one component fits into a "cam surface" or groove in another component, in particular in order to effect a seal against a seal or gasket.

"Connected" and "coupled" refer to components that are either directly connected or coupled to another element or which are separated by intervening elements. When an element is referred to as being "directly connected" or "directly coupled" to another element, there are no intervening elements present.

"Comprise" and variations of the term, such as "comprising" and "comprises," are not intended to exclude other additives, components, integers or steps. "Elastic" refers to a material or component which can be bent or otherwise deformed elastically by a predetermined force but which will return to its original shape when the applied force is removed.

"Elastic" refers to a material or component which can be bent or otherwise deformed elastically by a predetermined force but which will return to its original shape when the applied force is removed.

"Elastomer" and "elastomeric" refer to an elastic polymer material such as natural rubber, silicone, silicone rubber, and the like.

"Elongated" refers to a configuration or shape having a length which is longer than its width.

"Flange" refers to a projecting rim, collar, or ring on a structural element of a component of the present device which supports or provides a place of attachment for other components.

"Fluid conduit" and "conduit" refer to a structure for receiving and/or transferring fluids, for example medical tubing, a catheter, a drain tube, an access port, or a needle.

"Inward" and "inwardly" mean in a direction toward the longitudinal axis or center of the present device or of a component part.

"Longitudinal" refers to a direction or orientation aligned with the length (longer portion) of the present device or a component thereof.

"Male Luer member" refers to a component of the present device comprising a projecting conduit having an open distal (outer) end and which tapers toward its distal end in order to allow connection to another fluid conduit.

"Outward" and "outwardly" mean in a direction away from the longitudinal axis or center of the present device or of a component part.

"Rim" refers to an outer edge of a component of the present device.

Relative terms, such as "lower", "bottom", "below", "upper", "top" or "above," may be used herein to describe one element's relationship to another element as illustrated in the Figures. Such relative terms are intended to encompass different orientations of the device in addition to the orientation depicted in the Figures.

Luer Connector

Figure 3A:
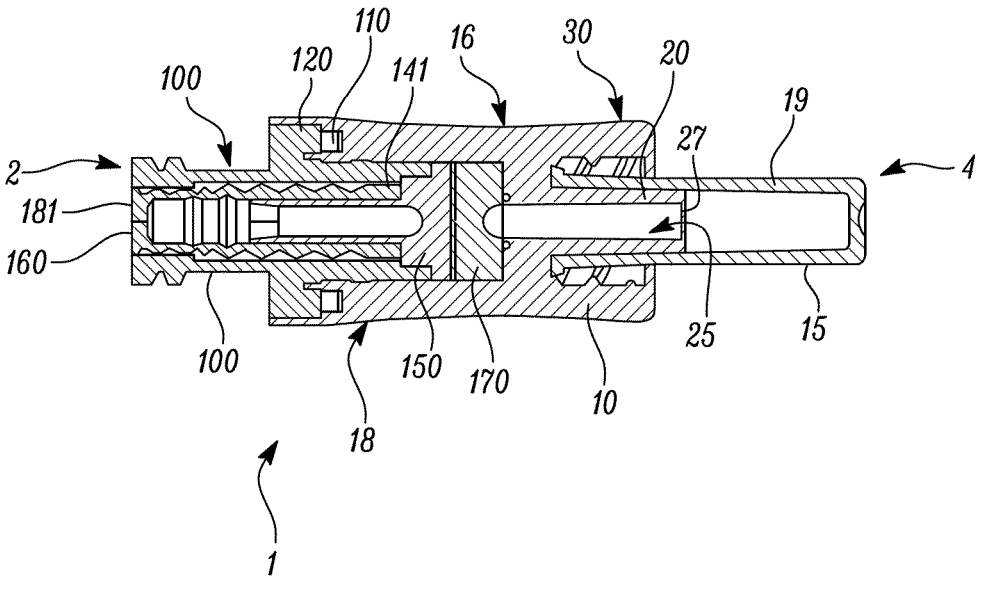
Fig. 3) means that the drawing applies to each of the embodiments.
Figure 3B:
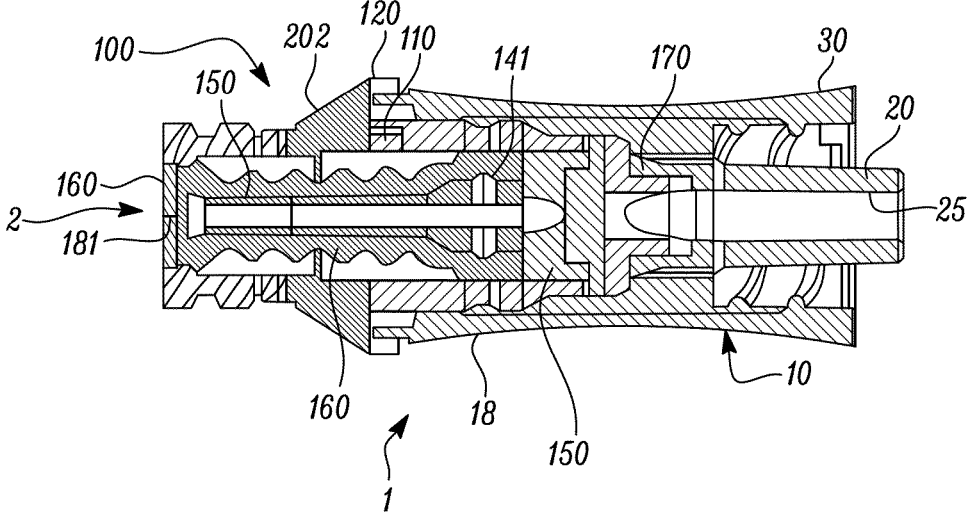
Figure 3C:
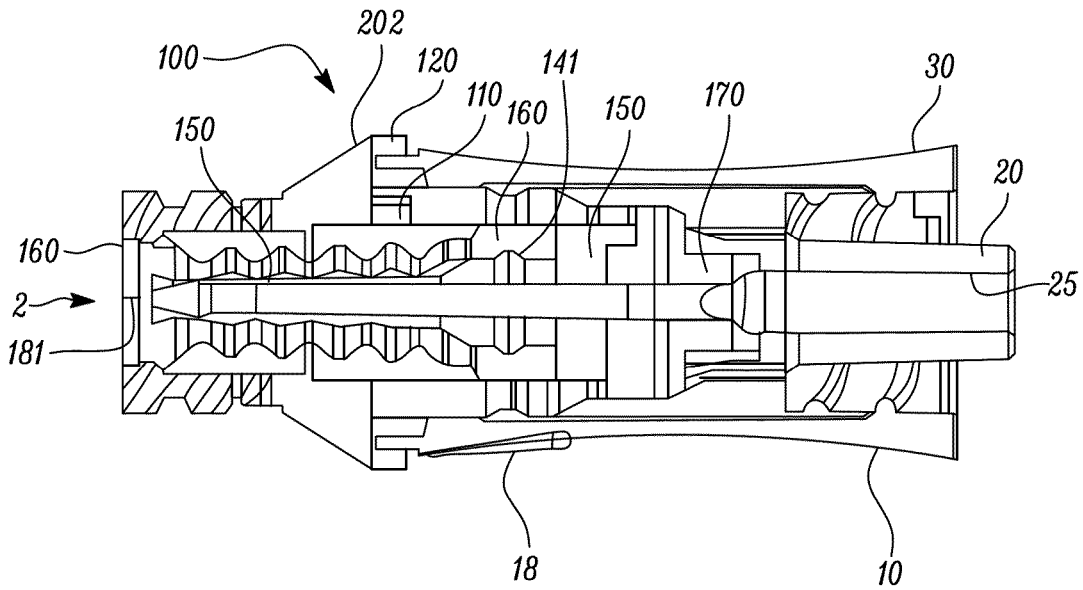
Figure 4A:
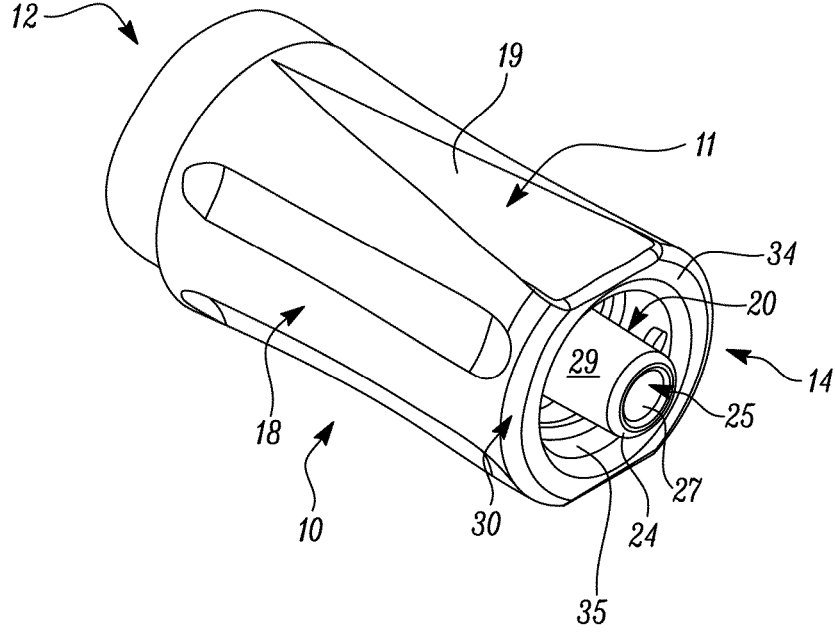
FIGS. 4 A & B/C are each a perspective view of the male Luer component of the present Luer connector.
Figure 10A:
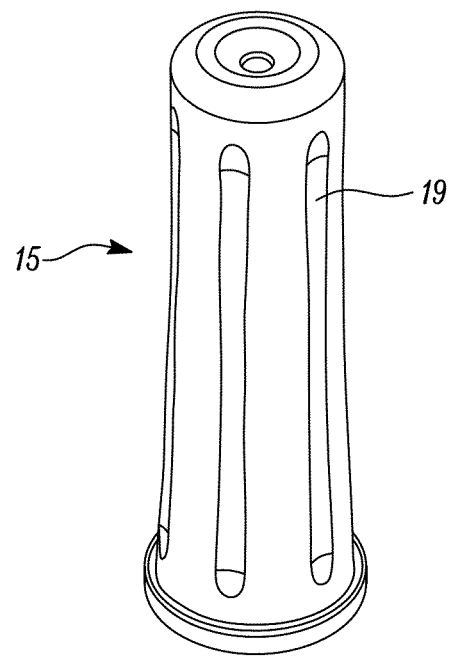
FIGS. 10 A is each a perspective view of a contamination cap for the male Luer component of the present Luer connector.
Figure 11A:
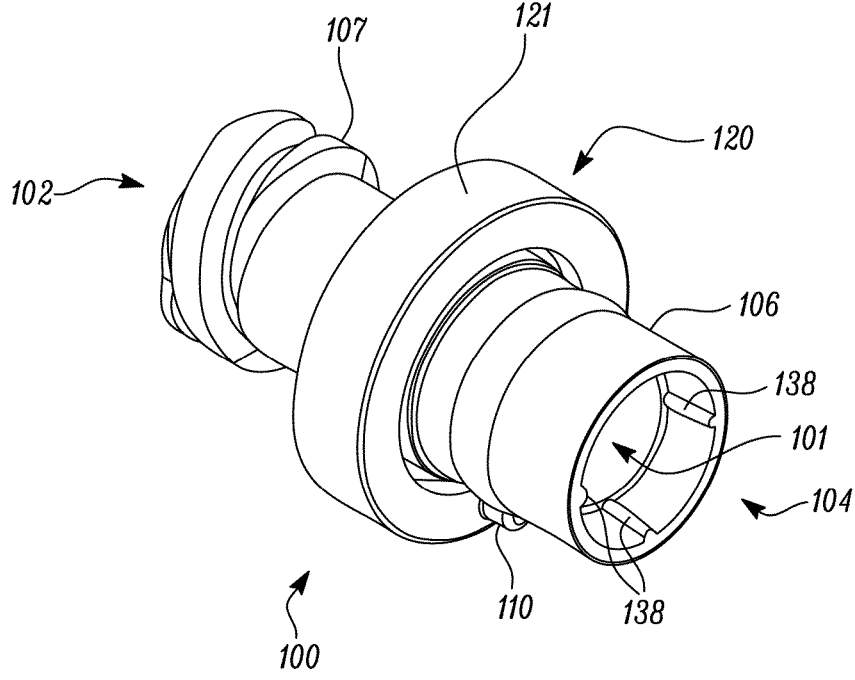
FIGS. 11 A & B/C are each a perspective view of the female Luer component of the present Luer connector.
Figure 12A:
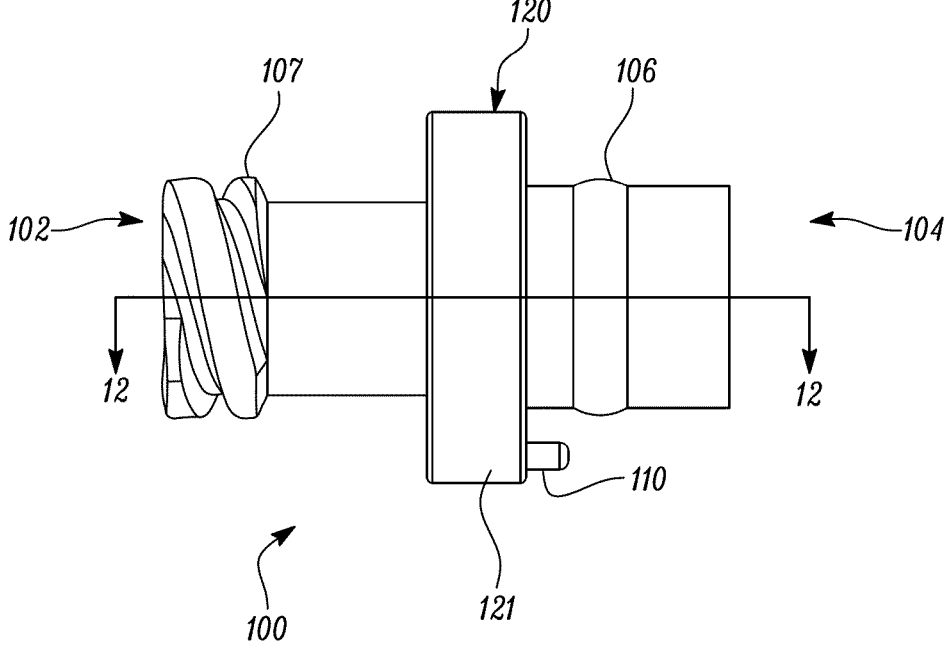
FIGS. 12 A & B/C are each a side elevation view of the female Luer component of the present Luer connector.

FIGS. 1A-3B/C illustrate the present connector assembly 1. The assembly comprises a female Luer body 100 in a proximal portion 2 of the assembly 1 and a male Luer body 10 in a distal portion 4. As shown in FIGS. 1A and 3A, the distal portion 4 optionally includes a cap 15 for covering a male Luer member 20. The cap 15 includes a tapered inner surface 18 in order to mate with the exterior surface of the male Luer member 20, and in heat-sterilized embodiments also preferably includes vents 16 (see FIG. 10A). As shown in FIGS. 3A-3C, the assembly 1 further includes a seal 170 and a channel insert 150, which together with the male Luer body 10 forms a flow channel for fluids being transferred through the connector 1.

Male Luer Body

The male Luer body 10 of the present connector assembly 1 is shown in FIGS. 4A-9A. The male Luer body 10 includes a proximal end 12, a distal end 14, an upper side 11, a lower side 13, and two lateral sides 16 and 18. The upper side 11 and/or lower side 13 preferably include a relatively flat, planar portion 19 in order to allow better gripping of the assembly 1 when being handled by a user, particularly when it is necessary to turn or twist the assembly 1, and to deter rolling of the male Luer body 10 when placed on a flat surface. In the illustrated embodiments, the planar portion 19 is triangular in shape, i.e. such that one longitudinal end is visually distinguishable from the other longitudinal end, in order to facilitate the orientation of the connector assembly 1, though other non-symmetrical shapes can also be used. At the distal end 14, the male Luer body 10 includes a longitudinally projecting male Luer member 20 having a proximal end 22 and a distal end 24. The male Luer member 20 comprises an inner lumen 25. The proximal end 22 comprises a proximal opening 23 at one end of the lumen 25, and the distal end 24 comprises a distal opening 27 at the other end, which together form a portion of the fluid flow path through the present connector assembly 1. The diameter of the outer surface 29 of the male Luer member 20 decreases from the proximal end 22 to the distal end 24 in order to form a taper.

The distal end 24 of the male Luer member 20 preferably extends longitudinally beyond the distal end 34 of an annular, preferably circumferential flange or collar 30 which surrounds the male Luer member 20. Between the distal end 34 and the proximal end 32 of the collar 30, the inner surface 35 is preferably provided with grooves 37 to engage the threads of another fluid transfer device to which the present connector assembly 1 can be connected to form a fluid flow path.

At the distal end 24 of the male Luer member 20, the male Luer body 10 comprises a receptacle 40 for receiving the female Luer assembly 105 having a proximal end 42, a distal end 44, and an inner surface 45. The distal end 44 includes seal pegs 41 and an O-ring groove 49 for retaining a seal 170 in the receptacle 40. In the first embodiment, there were provided three seal pegs 41 angularly equidistantly about the distal end 44 and a locator peg 41L for properly angularly orientating the seal 170 during assembly. In the second and third embodiments, two seal pegs 41 are provided along with a considerably wider locator peg 41L to facilitate easier orientation during assembly.

Figure 5A:
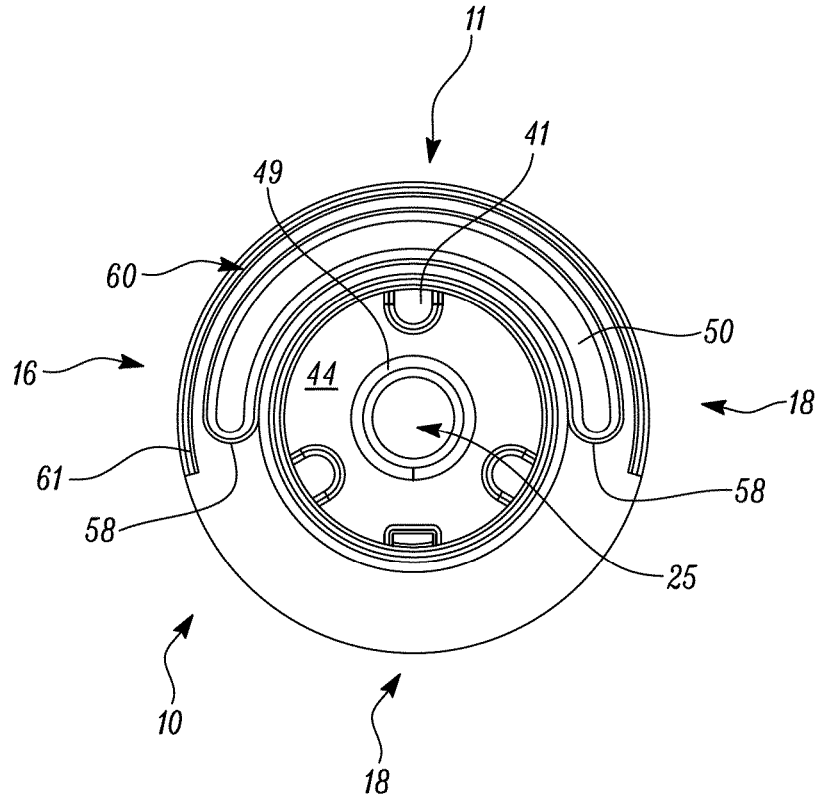
FIGS. 5 A & B/C are each a rear elevation view of the male Luer component of the present Luer connector.
Figure 6A:
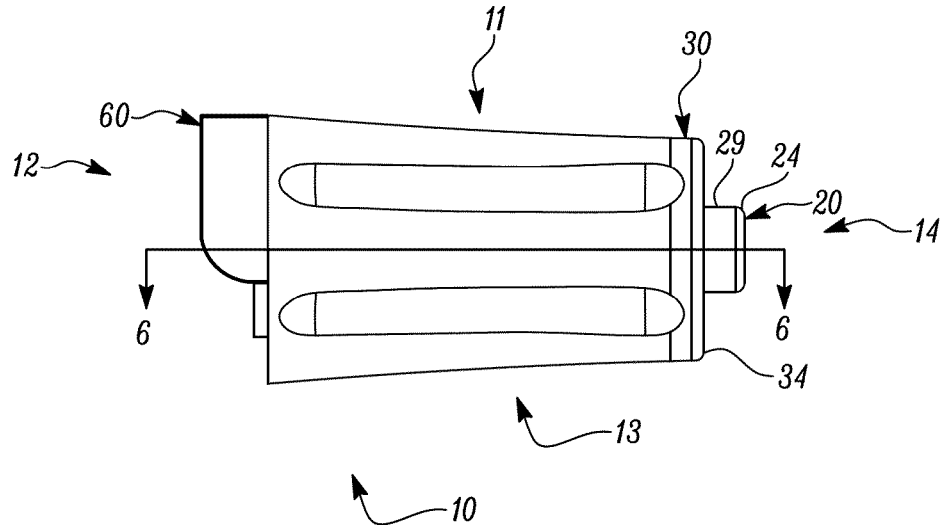
FIGS. 6 A & B/C are each a side elevation view of the male Luer component of the present Luer connector.
Figure 7A:
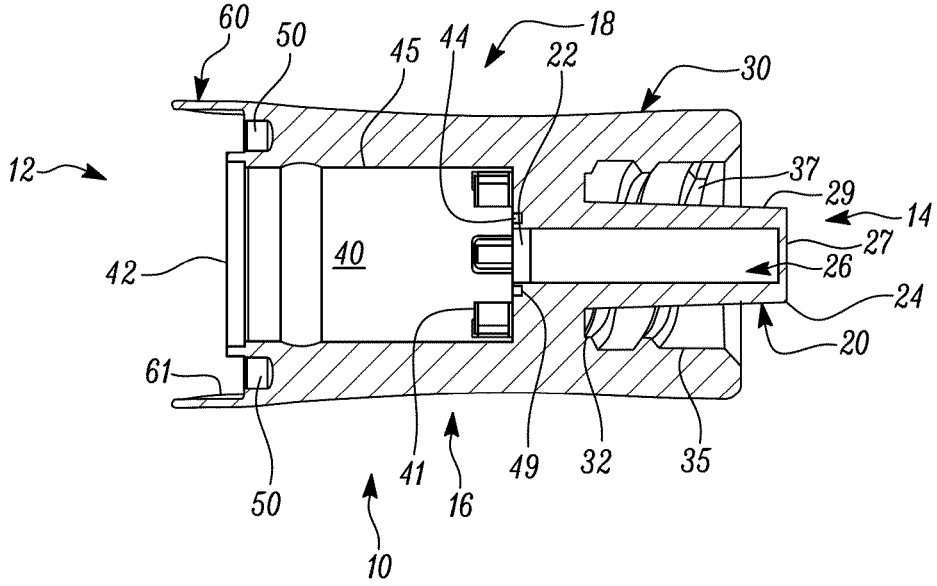
FIGS. 7 A & B/C are each a sectional view of the male Luer component of the present Luer connector along line 6-6 of FIG. 6.
Figure 8A:
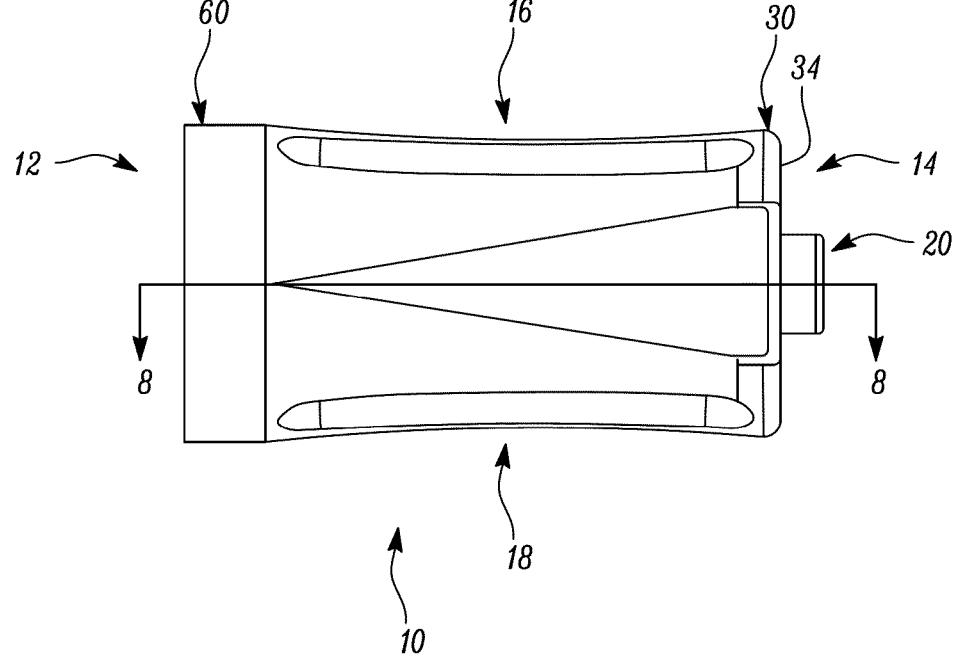
FIGS. 8 A & B/C are each a top plan view of the male Luer component of the present Luer connector.
Figure 9A:
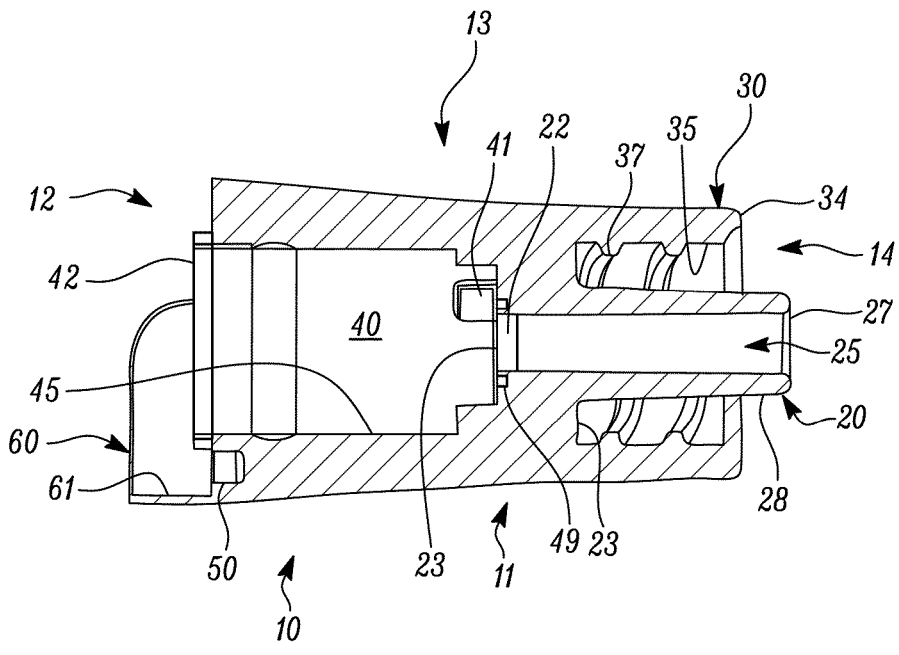
FIGS. 9 A is each a sectional view of the male Luer component of the present Luer connector along line 8-8 of FIG. 8 A.

The proximal end 12 of the male Luer body 10 further includes an annular, semi-circular cam groove 50. As best seen in FIGS. 5A-5B/C, the cam groove 50 extends around a portion of the circumference of the proximal end 12 of the male Luer body 10, and is shaped to receive and cooperate with a cam post 110 on the female Luer body 100. In the second and third embodiments, there is additionally provided a protrusion 50P extending into the cam groove 50 at each end thereof that are engaged by a longitudinally-extending cam post 110 on the underside of the female Luer body 100 in alignment therewith. The cam post 110 rides in the cam groove 50 and snaps over the protrusions 50P to provide increased turning resistance to assure that the valve 1 is rotated open once the male Luer connection (e.g., from an intravenous line) is fully connected to the connector 1 and conversely, to assure that the valve 1 is rotated closed before the male Luer connection is disengaged. The protrusions 50P also provides a tactile indication to the nurse indicating when the male Luer connection is fully engaged or disengaged from the valve 1 as the valve opens or closes, respectively.

In the first embodiment, the proximal end 12 of the male Luer body 10 also preferably comprises a semi-circular, annular guard or shield 60 which extends around a portion of the periphery of the proximal end 12 and has an inner surface 61. The guard 60 extends longitudinally and proximally of the proximal end 42 of the receptacle 40, in order to help prevent unintentional rotation of the female Luer body 100, which might accidentally disconnect it from the male Luer body 10. This is a particular issue when users are wearing protective gloves, which decrease the dexterity of the user. The guard also helps to prevent externally spilled fluid from getting in between the female Luer body 100 and the male Luer body 10. In the second and third embodiments, the annular guard shield extends 360 degrees around the periphery of the proximal end 12.

Female Luer Assembly

The receptacle 40 of the male Luer body 10 (see FIG. 7A) is adapted to receive a female Luer assembly 105. The female Luer assembly 105 (FIGS. 15A-20C) includes a female Luer body (FIGS. 11A-14C), a seal 170 (FIGS. 28A-32B/C) at the distal end 44 of the receptacle 40, a channel insert 150 (FIGS. 21A-25A) adjacent the seal 170, and a stopper 160 (FIGS. 26A-27B/C) at the proximal end 42 of the receptacle 40.

As best seen in FIGS. 11A-14B/C, the female Luer body 100 comprises a proximal end 102, a distal end 104, and an interior 101 for retaining the channel insert 150 and stopper 160 (as shown in FIGS. 19A-20C). Proximal end 102 preferably includes threads 107 for mating with the grooves of another fluid transfer device. The distal end 104 of the female Luer body 100 is adapted to fit within the receptacle 40 of the male Luer body 10. When the female Luer body 100 is retained within the male Luer body, the outer surface 106 of the proximal end 104 is adjacent to, and preferably is in contact with, the inner surface 45 of the receptacle 40 of the male Luer body 10 (FIG. 3A).

Figure 13A:
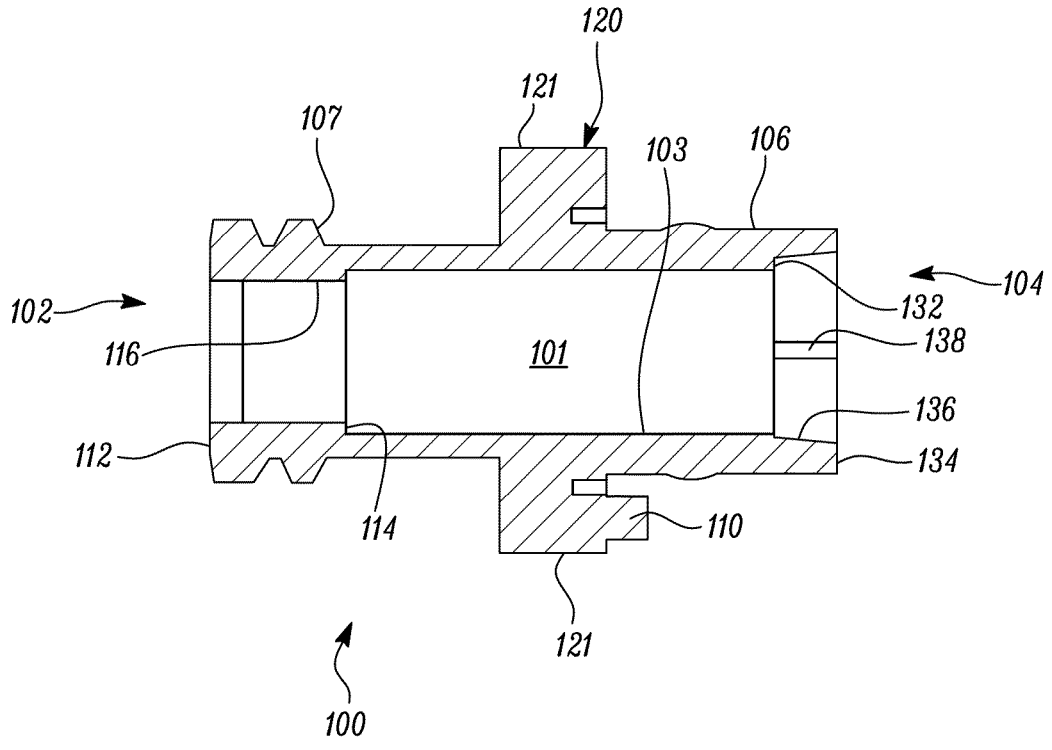
FIGS. 13 A & B/C are each a sectional view of the female Luer component of the present Luer connector along line 12-12 of FIG. 12.
Figure 14A:
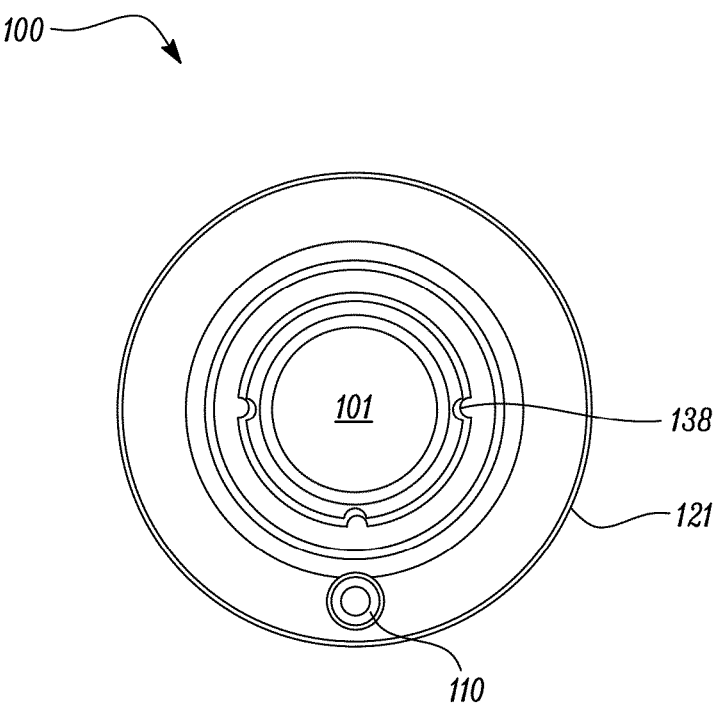
FIGS. 14 A & B/C are each an elevation view of the distal end of the female Luer component of the present Luer connector.
Figure 15A:
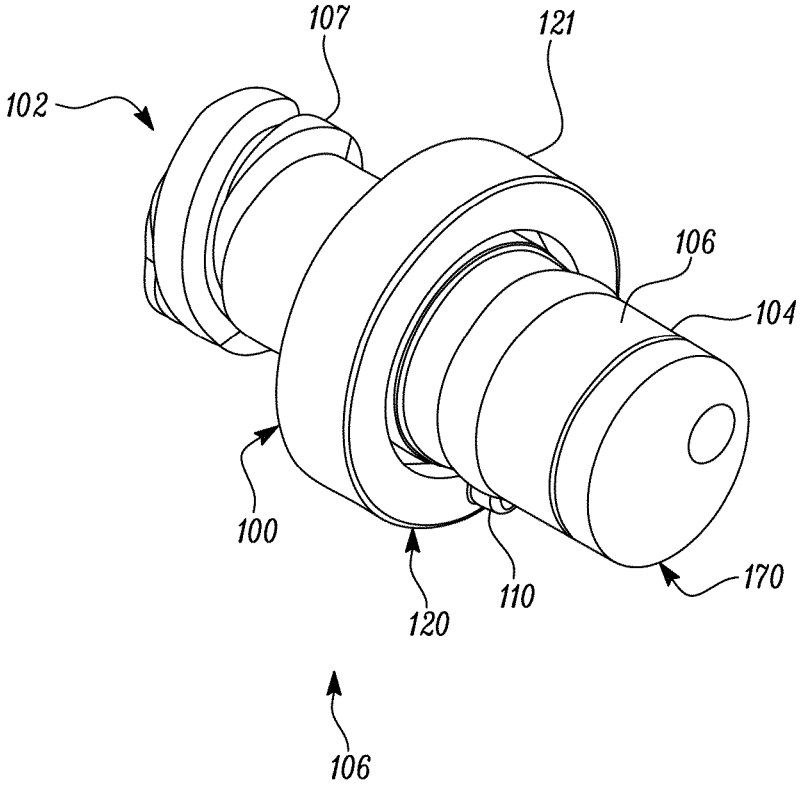
FIGS. 15 A & B/C are each a perspective view of the female Luer assembly of the present Luer connector.
Figure 16A:
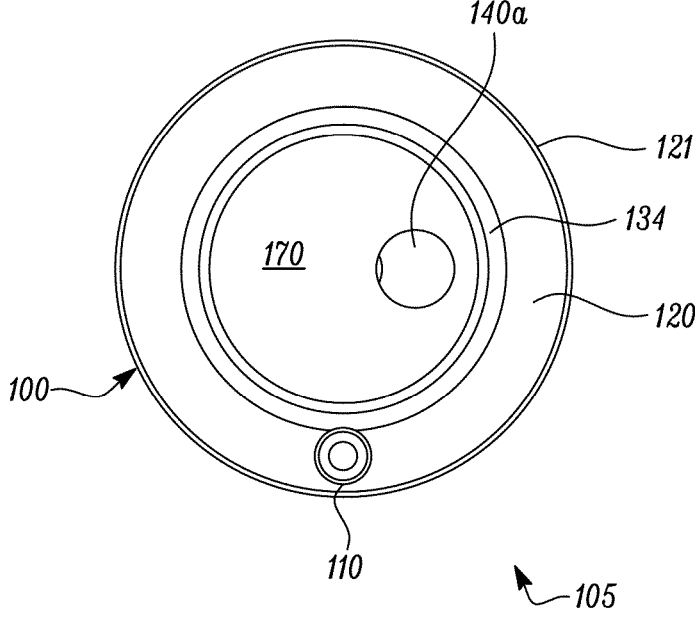
FIGS. 16 A & B/C are each a front elevation view of the female Luer assembly of the present Luer connector.
Figure 17A:
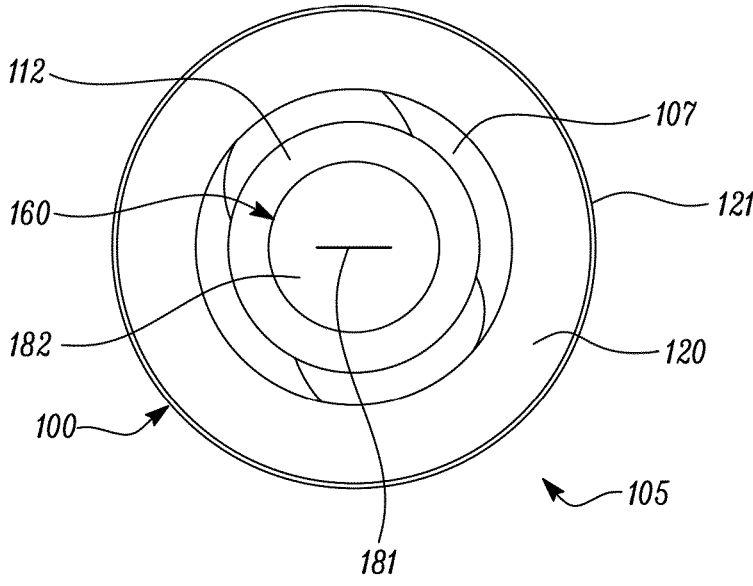
FIGS. 17 A are each a rear elevation view of the female Luer assembly of the present Luer connector.
Figure 18A:
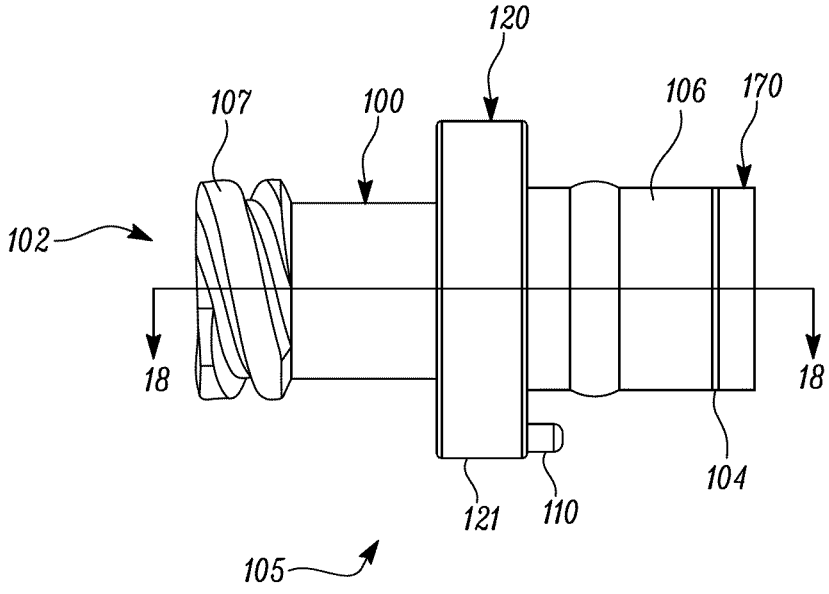
FIGS. 18 A & B/C are each a side elevation view of the female Luer assembly of the present Luer connector.
Figure 19A:
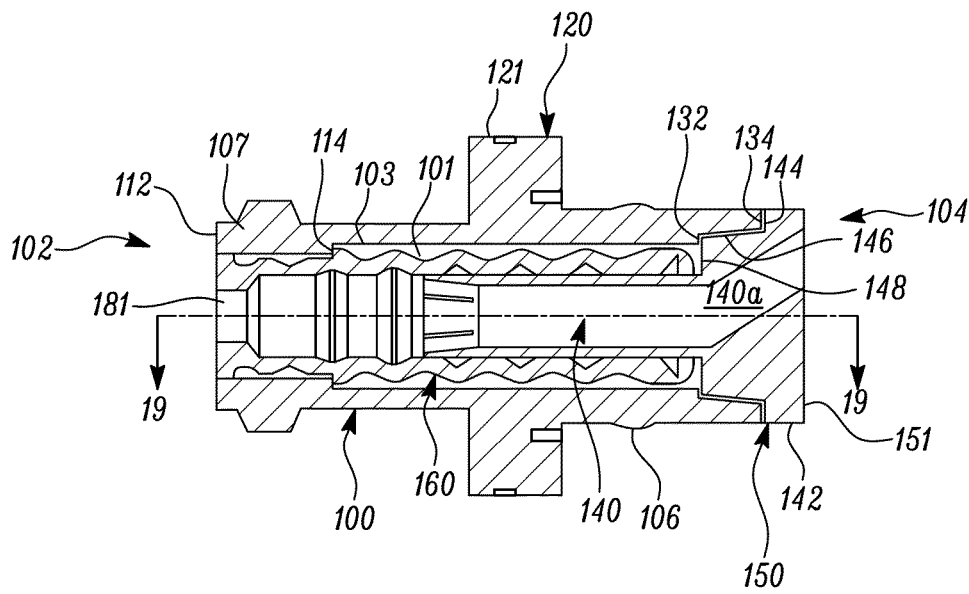
FIGS. 19 A, B & C are each a sectional view of the female Luer component of the present Luer connector along line 18-18 of FIG. 18.
Figure 19B:
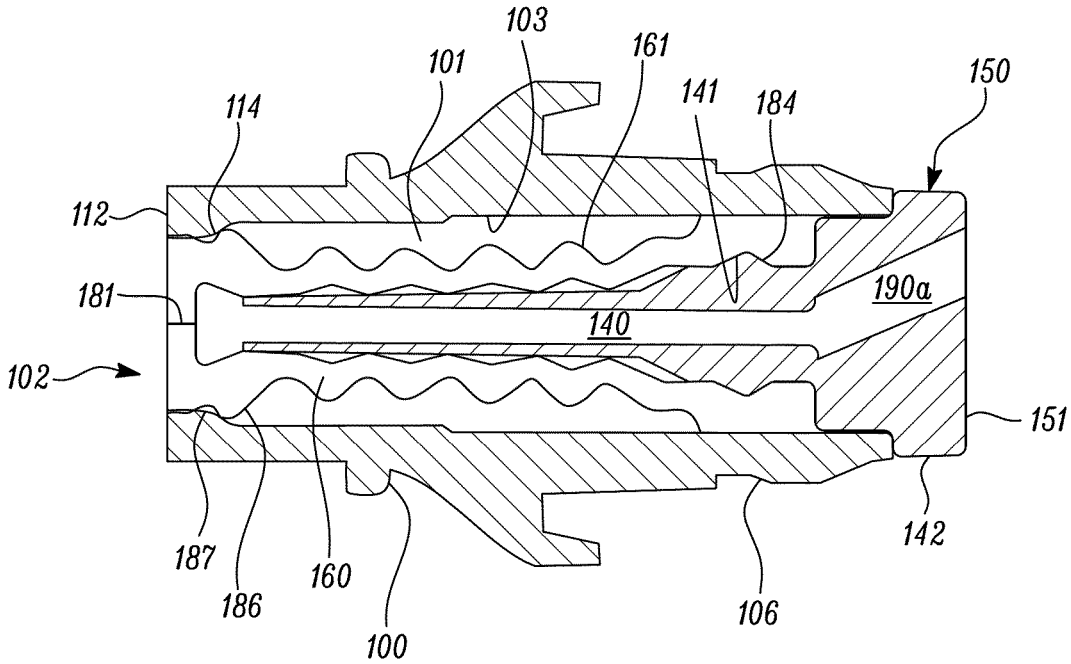
Figure 19C:
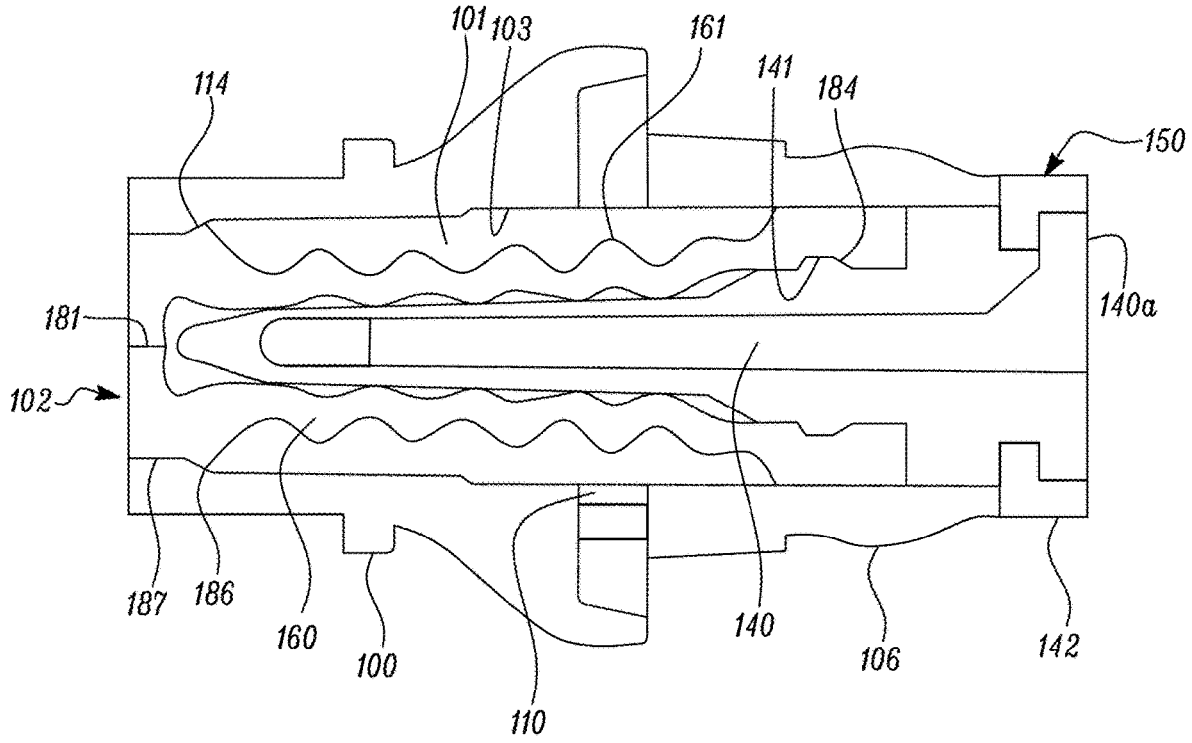
Figure 20A:
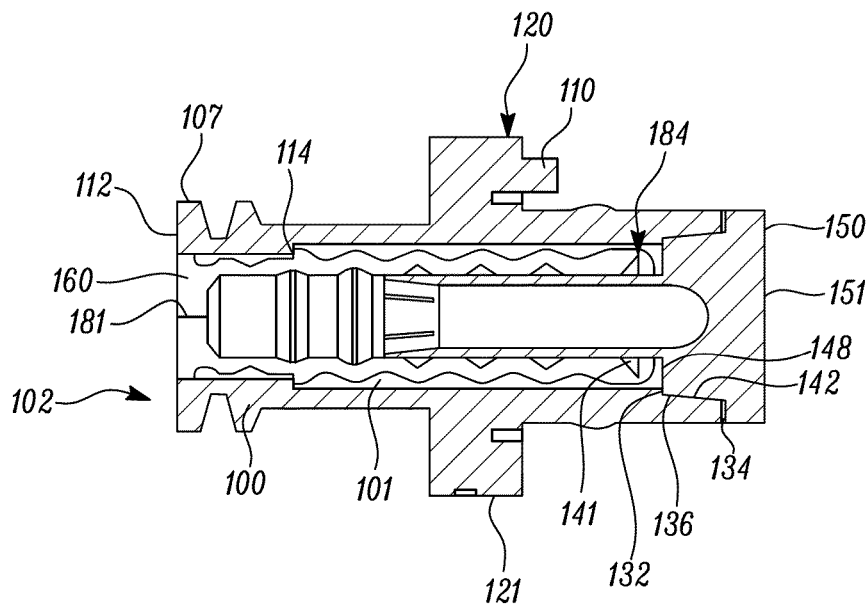
FIGS. 20 A, B & C are each a sectional view of the female Luer component of the present Luer connector along line 19-19 of FIG. 19.
Figure 20B:
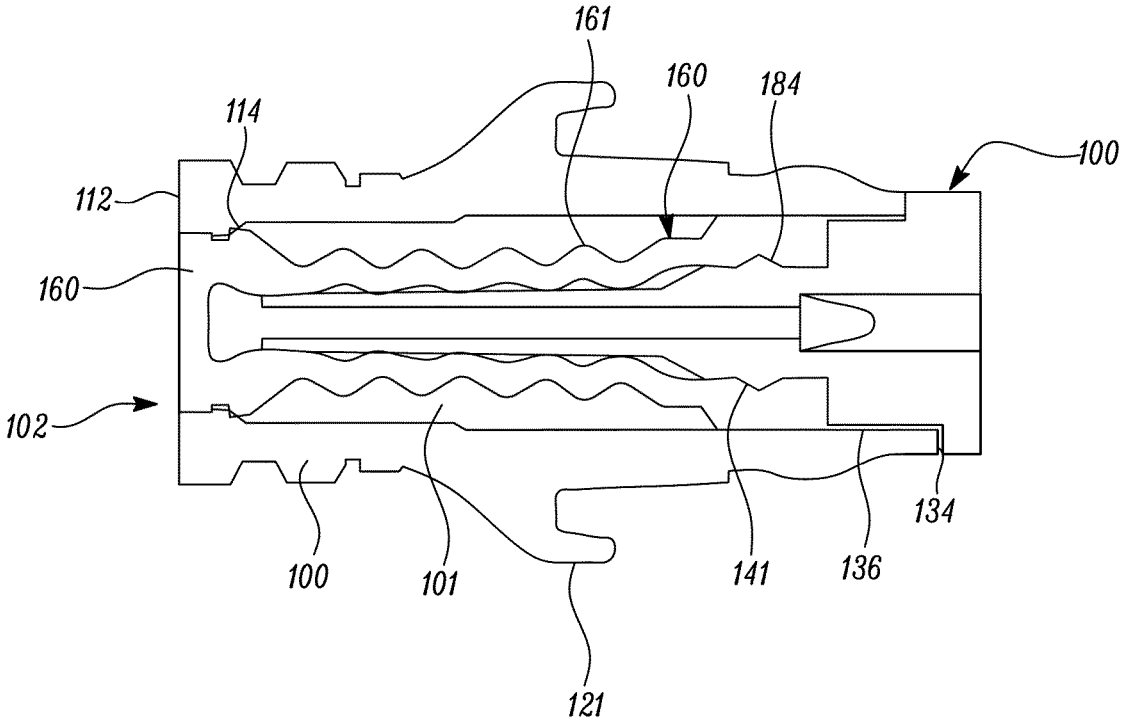
Figure 20C:
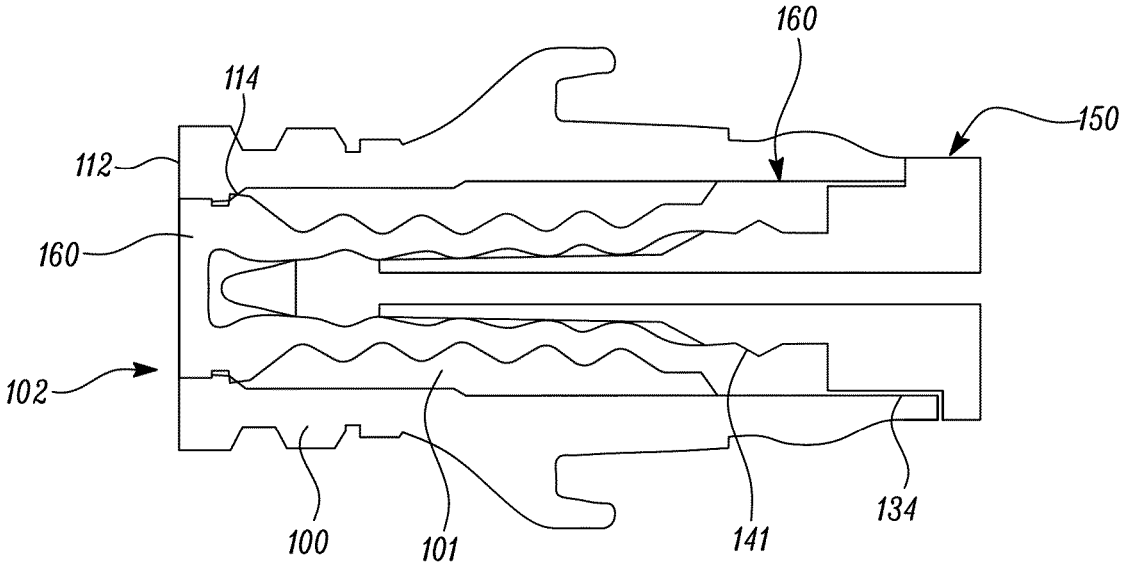
Figure 21A:
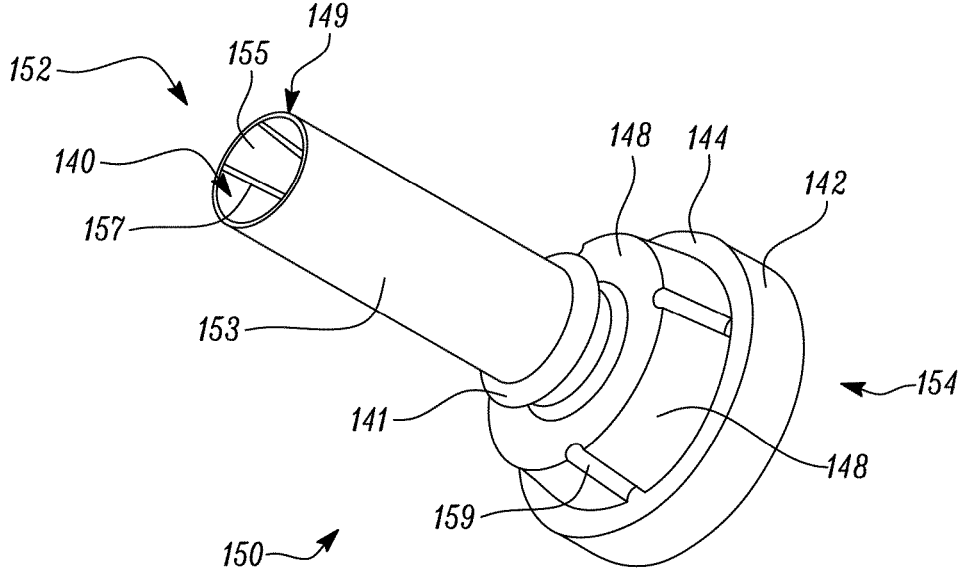
FIGS. 21 A, B & C are each a perspective view of the channel insert of the female Luer assembly of the present Luer connector.
Figure 21B:
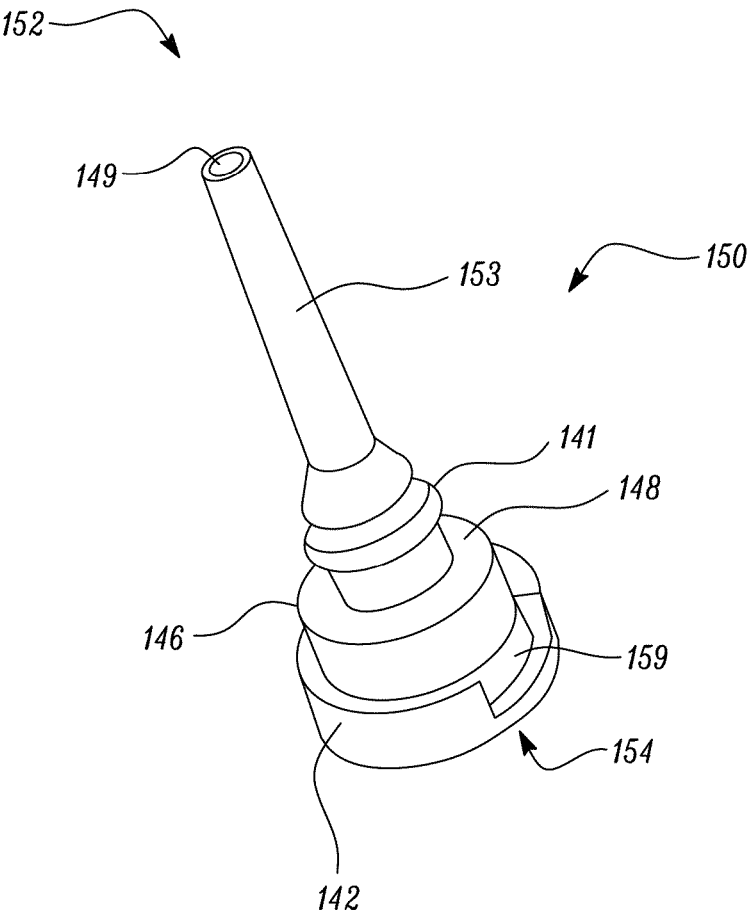
Figure 21C:
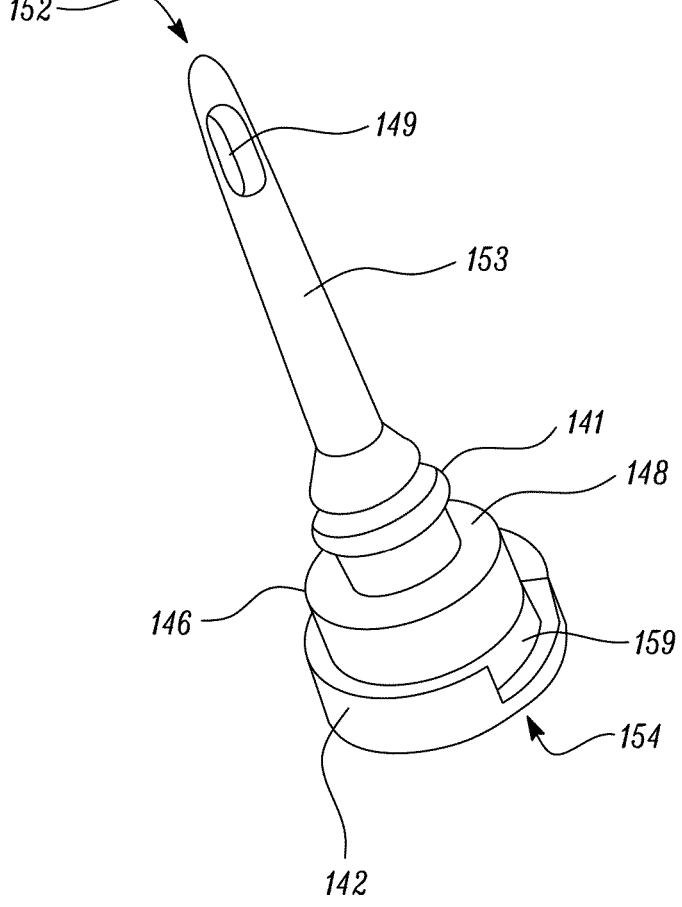
Figure 22A:
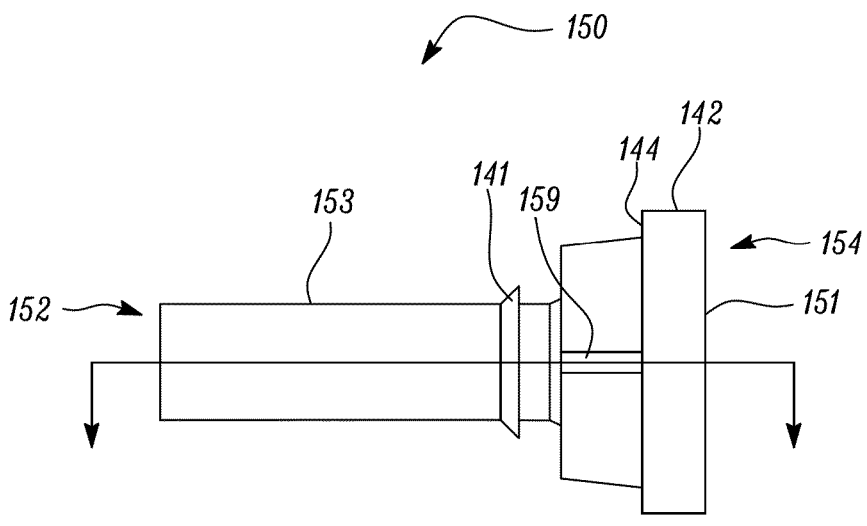
FIGS. 22 A, B & C are each a side elevation view of the channel insert of the female Luer assembly of the present Luer connector.
Figure 22B:
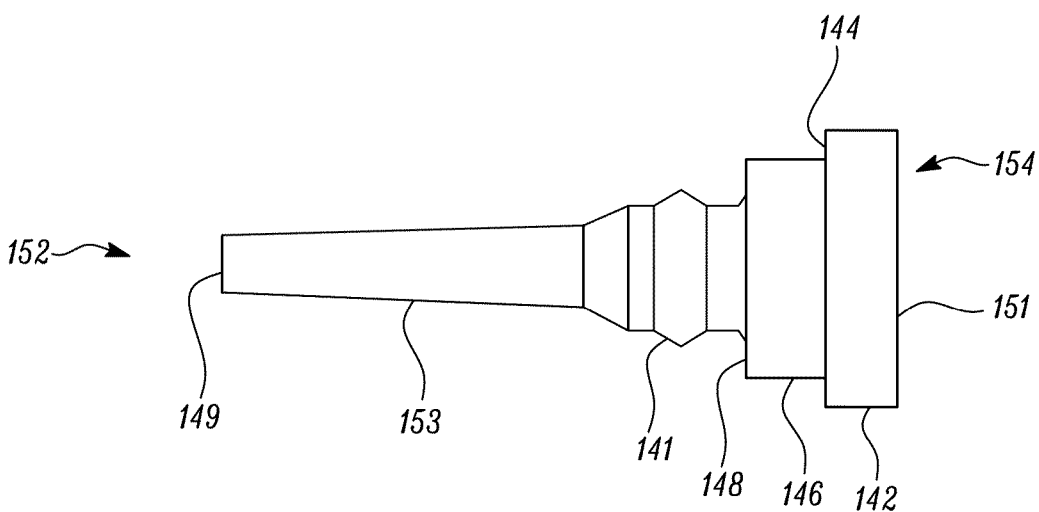
Figure 22C:
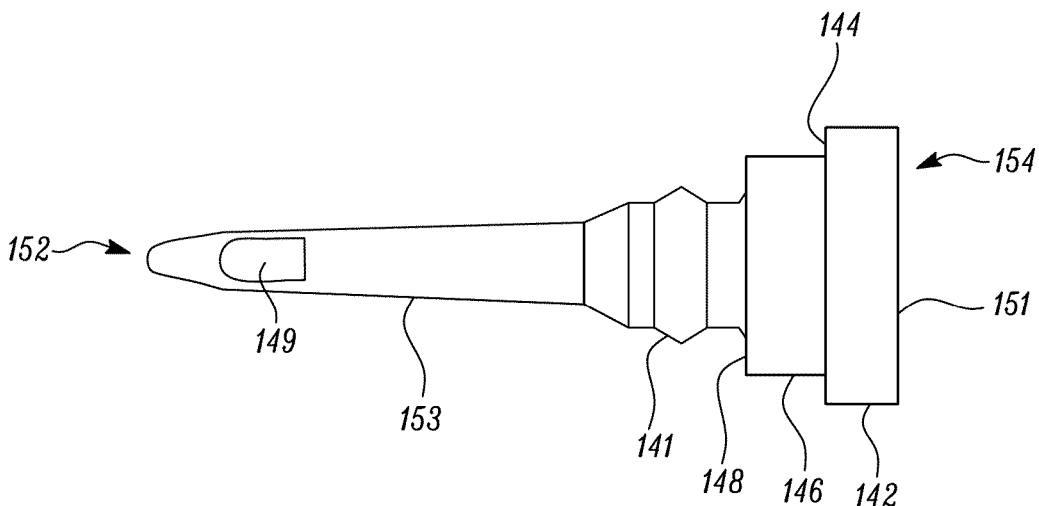

As best seen in FIG. 13A, the interior 101 of the female Luer body 100 comprises an inner surface 103 for retaining components of the female Luer assembly 105. At proximal end 102, the interior 101 includes an inwardly extending annular wall or surface 114 which extends inwardly from a proximal end of the inner surface 103. This inwardly extending wall 114 helps to retain the elastomeric stopper 160 (as described further below). In the first embodiment, a proximal inner surface 116 extends proximally from the inwardly extending wall 114 toward the proximal end 102, ending at exterior proximal surface 112. At a distal end of the inner surface 103, and outwardly extending annular wall or surface 132 extends outwardly, in order to help retain the channel insert 150. A distal inner surface 136 frusto conically extends distally from the outwardly extending surface 132, ending as an exterior distal surface 134.

The female Luer body 100 preferably includes a cam post 110 which rides in the cam groove 50 of the male Luer body 10. The cam post 110 allows the female Luer body 100 to be rotated until the cam post 110 reaches one of the lateral ends 56 or 58 of the cam groove 50 (FIG. 5A), thereby preventing over-torqueing of the female Luer body 100.

In the first embodiment, the cam post 110 and cam groove 50 could also cooperate to prevent separation of the male Luer body 10 and the female Luer body 100 under conditions of high pressure. The cam post 110 extends longitudinally toward the distal end 104 of the female Luer body 100 from an annular, preferably circumferential flange 120 extending outwardly from a medial portion of the female Luer body 100. The flange 120 facilitates rotation of the female Luer body 100 when attaching it to or detaching it from the male Luer body 10 (at the distal end 104) and/or another fluid transfer device (at the proximal end 102). The outer surface 121 of the flange 120 preferably abuts the inner surface 61 of the guard 60 of the male Luer body 10 when the male Luer body 10 and female Luer body 100 are connected.

In the second and third embodiments, the flange 120 extends over the proximal end 12 of the male Luer body 10 and the cam post 110 is positioned underneath the flange 120.

As best seen in FIGS. 19A-20C, the female Luer body 100 engages and retains a channel insert 150, which is shown in FIGS. 21A-25A. A channel insert 150 generally comprises a proximal end 152, a distal end 154, and an interior channel 140 extending between the proximal end 152 and the distal end 154. The proximal end 152 of the channel insert 150 generally comprises a preferably tubular conduit 153 having an opening 149 at its proximal end.

In the first embodiment, at or adjacent the opening 149, the interior surface 155 of the channel 140 preferably comprises generally longitudinally extending grooves 157. The distal end 154 of the channel insert 150 includes an outwardly extending medial surface or wall 148, which extends outwardly from the outer surface of the conduit 153. The outwardly extending medial wall 148 meets an annular medial surface or wall 146, which extends generally frustro-conically (longitudinally and distally) to an outwardly extending distal wall 144. At the outer perimeter of the outwardly extending distal wall 144, an annular distal surface or wall 142 extends outwardly to the distal surface 151 of the channel insert 150. An annular barb-shaped flange or ring 141 extends outwardly from the tubular conduit 153 between the outwardly extending medial wall 148 and the proximal end 152 of the channel insert 150.

In the second and third embodiments, the channel 140 is lengthened to extend to the inside end of the stopper 160. The annular medial surface or wall 146 is formed less frustro-conically. In both the first and second embodiments the channel 160 comprises a blunt end opening 149 whereas in the third embodiment, the channel 160 comprises a spiked end with opposing side openings 149 located immediately below its pointed tip. The extended-length channel 160 that extends to the end of the underside of the stopper 160 advantageously precludes a vacuum being established within the stopper 160 upon disengagement of the male Luer connector from the valve 1 that, in the case of the first embodiment, would sometimes hinder the stopper 160 from returning to its normal at rest closed position upon disengagement of the male Luer connector. With such a vacuum, the stopper 160 would need to "burp" to take in air to eliminate the vacuum, so that the stopper would return to its normal at rest closed position. Taking in air would then compromise the desired zero displacement feature of the valve 1.

Figure 23A:
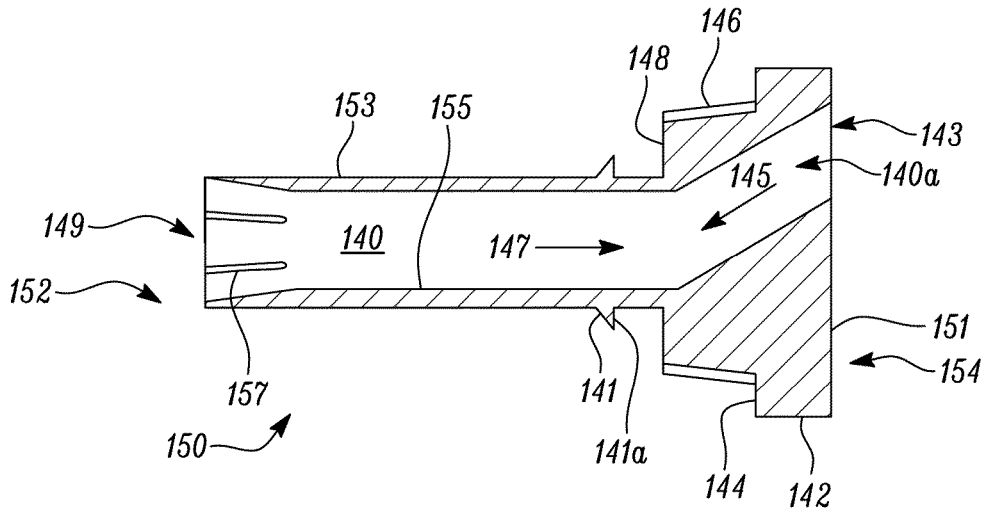
FIGS. 23 A, B & C are each a sectional view of the channel insert of the female Luer component of the present Luer connector along line 22-22 of FIG. 22.
Figure 23B:
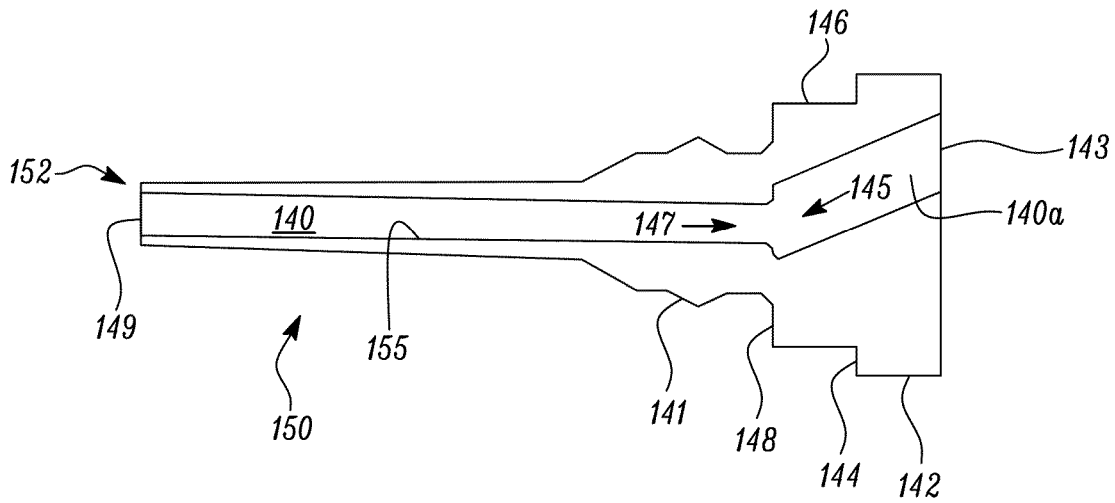
Figure 23C:
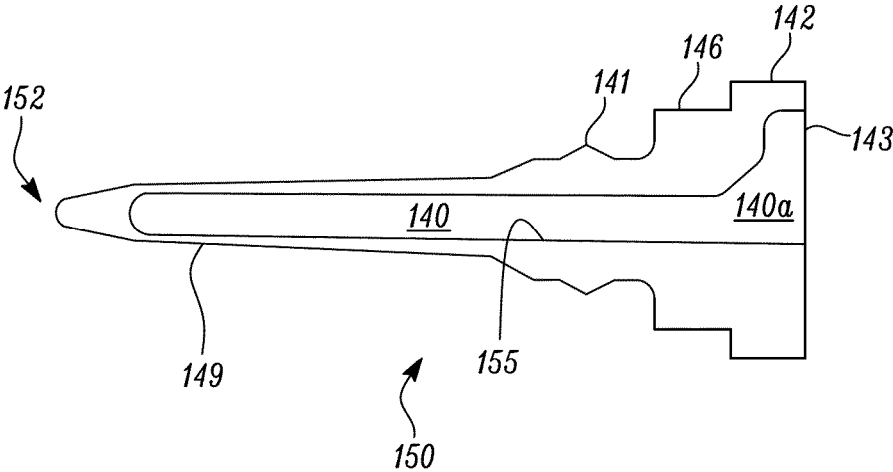
Figure 24C:
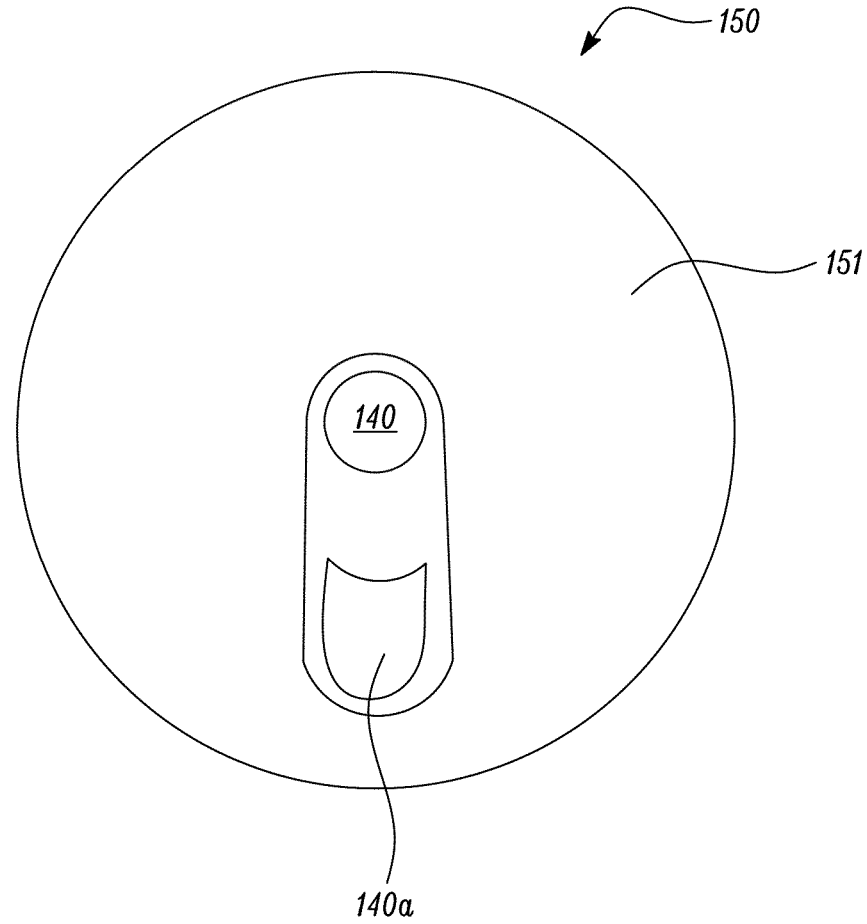
FIGS. 24 A/B & C are each a rear elevation view of the channel insert of the female Luer assembly of the present Luer connector.
Figure 25A:
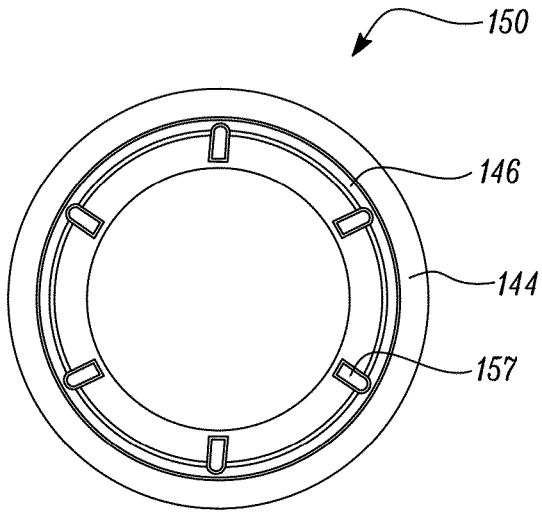
FIGS. 25 A is each a front elevation view of the channel insert of the female Luer assembly of the present Luer connector.
Figure 26A:
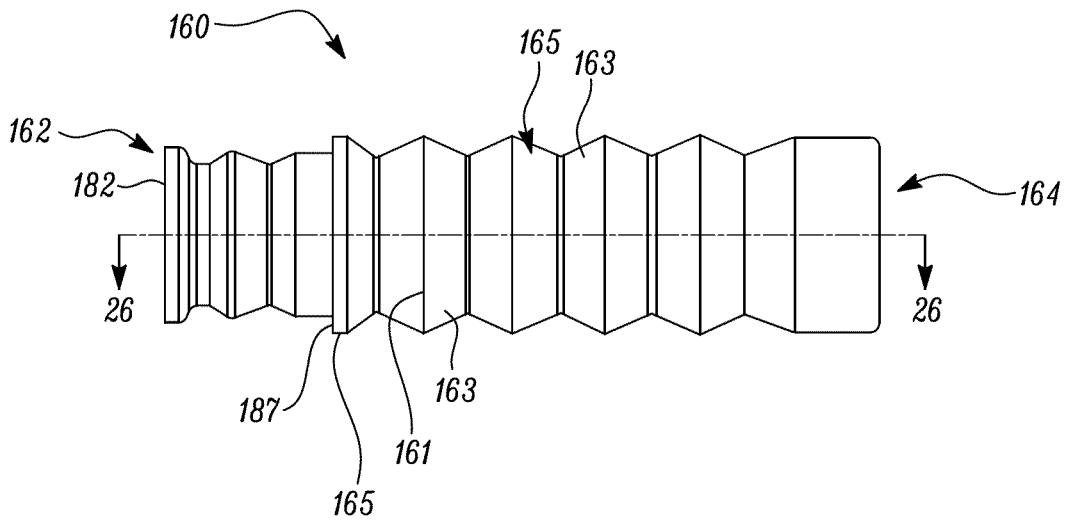
FIGS. 26 A & B/C are each a side elevation view of the elastomeric stopper of the female Luer assembly of the present Luer connector.
Figure 27A:
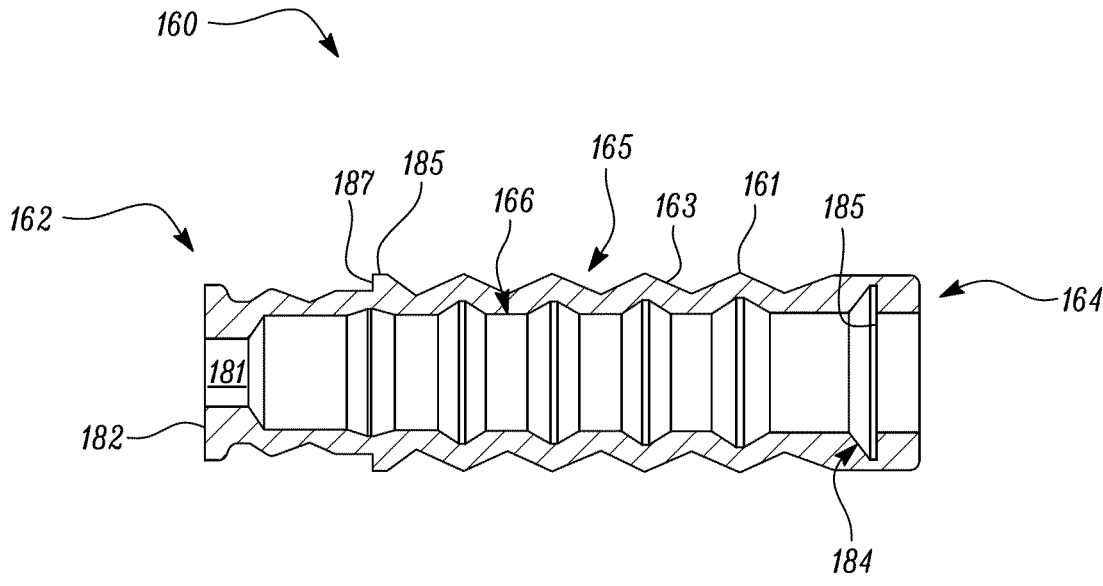
FIGS. 27 A & B/C are each a sectional view of the elastomeric stopper of the female Luer assembly of the present Luer connector along line 26-26 of FIG. 26.
Figure 28A:
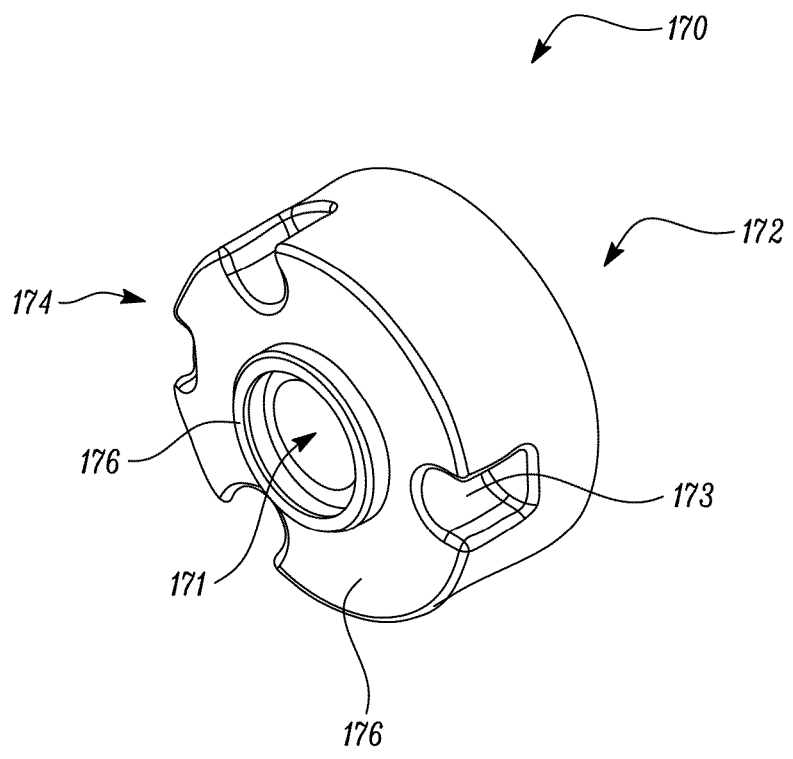
FIGS. 28 A & B/C are each a perspective view of the seal component of the present Luer connector.
Figure 30A:
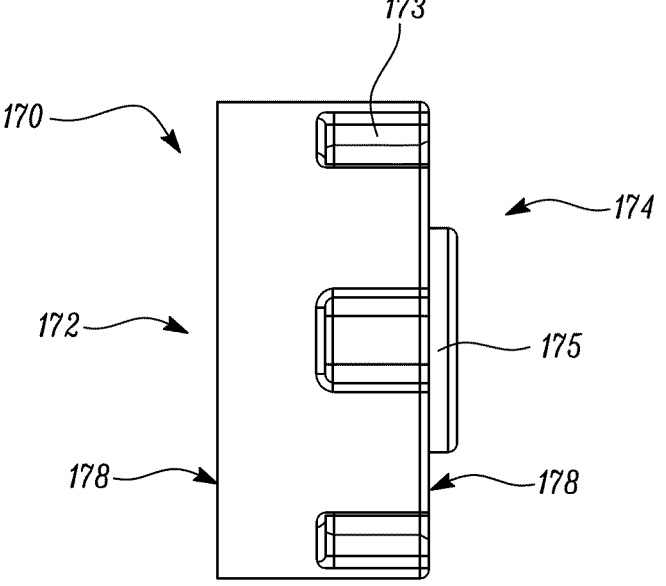
FIGS. 30 A is a side elevation view of the seal of the present Luer connector and FIG. 31 is a front elevation view of the seal of the present Luer connector.
Figure 31A:
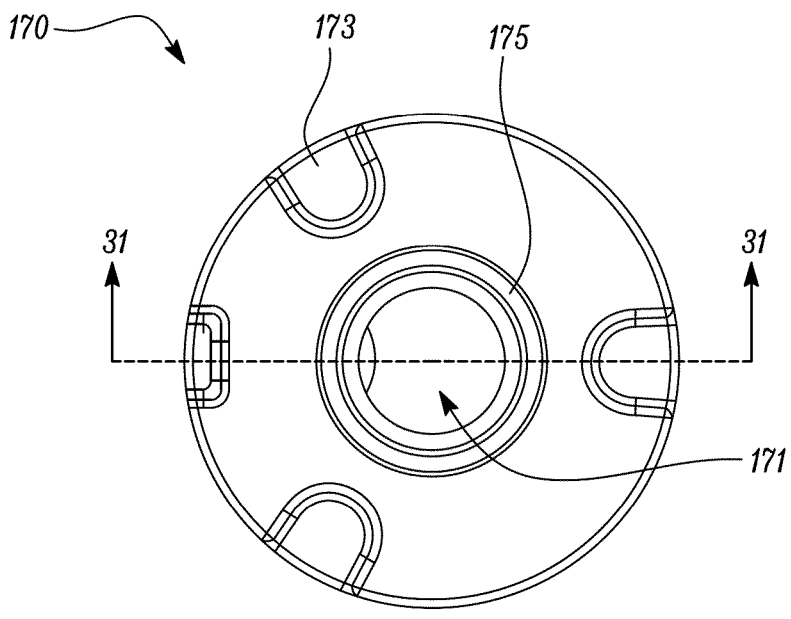
Figure 32A:
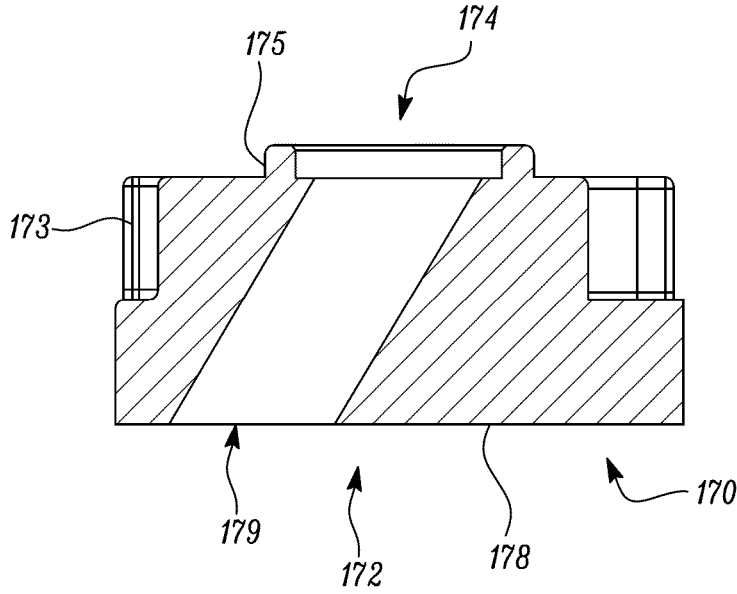
FIGS. 32 A & B/C are each a sectional view of the seal of the present Luer connector along line 31-31 of FIG. 31.

As best seen in FIG. 23A, the channel 140 extends from the opening 149 distally to a distal channel opening 147. The distal channel opening 147 meets and/or is integrally formed with a proximal side channel opening 145 for a side channel 140a. The distal channel 140a meets the interior channel 140 at an angle, in order to position the channel distal opening 143 away from the center of the distal surface 151 of the channel insert 150. The use of an offset opening 143 ensures that this opening aligns with the corresponding opening on the seal 170, thereby allowing fluid flow through the connector 1, only when the female Luer body 100 and the channel insert 150 which it retains are secured to the male Luer body 10. When the female Luer body 100 is not appropriately rotated and securely retained within the male Luer body 10, the opening 143 of the channel insert 150 will not align, or not fully align, with the corresponding opening 179 on the seal 170 and thereby block fluid flow through the valve 1. Blocking fluid flow through valve 1 is important to achieve a zero displacement valve 1 (i.e., a valve 1 that does not allow injection or withdrawal of fluid from the IV line or other component to which the valve 1 is connected when the access device is engaged or disengaged from the valve 1).

The distal end 104 of the female Luer body 100 generally engages the channel insert 150 at the distal end 154 of the channel insert 150. As seen for example in FIG. 19A, the exterior distal surface 134 of female Luer body 100 abuts distal wall 144 of the channel insert 150; distal inner surface 136 of the female Luer body 100 abuts the medial wall 146 of the channel insert 150; and outwardly extending surface 132 of the female Luer body 100 abuts medial wall 148 of the channel insert 150. In order to securely retain and orient the channel insert within the female Luer body 100, in the first embodiment, a plurality of longitudinal grooves 159 are provided on the medial wall 146 (see FIG. 21A) whereas in the second and third embodiments, there is only one, extra-wide longitudinal groove 159 and it is formed on the wall 142 instead of wall 146.

In the first embodiment, the grooves 159 are engaged by longitudinally extending projections or cams 138 on the distal inner surface 136 of the distal end of the female Luer body 100 (see FIGS. 11 and 13-14) whereas in the second and third embodiments, the single, wide groove 159 is engaged by a single extra-wide projection 138 longitudinally extending from the distal wall 134. In all embodiments, the projection(s) 138 prevent or resist rotational movement of the channel insert 150 when engaged by the groove(s) 159 of the channel insert 150.

A further advantage of the present channel insert 150 is that it prevents contact between the interior 101 of the female Luer body 100 and fluids passing through the connector assembly 1. This eliminates the possibility of contamination of such fluids due to contact with the interior 101.

The female Luer assembly 105 further comprises an axially (longitudinally) deformable elastomeric stopper 160, best seen in FIGS. 26A-27B/C. The stopper 160 generally comprises a hollow, longitudinal structure having bellows or accordion-like folds 161, with each fold being at the juncture of two opposed surfaces 163 on the exterior 165 of the stopper 160. The stopper is mounted or positioned around the channel insert 150, such that the interior surface 166 of the stopper 160 surrounds the exterior surface of the tubular conduit 153 of the channel insert (as seen in FIGS. 3A-3C, 19A-19C, and 20A-20C, for example). When force is exerted against the closed, proximal face 182 of the stopper 160 by a syringe or other fluid transfer device, the proximal face 182 is urged distally toward the proximal end 152 of the channel insert 150, and the opposed surfaces 163 of the accordion-like outer surface 165 are urged together, thereby collapsing the stopper 160 and reducing it in length. This allows a syringe, for example, to be inserted into the proximal end of the female Luer body 100.

In the first embodiment, when the proximal end 162 of the stopper 160 reaches the proximal end 152 of the channel insert 150, the syringe will push the elastic material of the proximal face 182 into the opening 149 of the channel 140 of the channel insert 150. The elastic material of the proximal face 182 will be urged into the longitudinally extending grooves 157 of the channel insert 150, which thereby grip the material of the stopper 160. The stopper 160 will resist twisting when gripped in this way, which is advantageous because twisting tends to weaken and/or tear the material, creating a risk of introducing an infection.

In the second embodiment, since the opening 149 is positioned immediately underneath the inner surface of the proximal end 162 of the stopper 160, the syringe immediately pushes the elastic material of the proximal face 182 over the opening 149 of the channel 140 so that the slit 181 immediately opens to encircle the channel 140 and form a seal therewith, thereby establishing fluid flow path between the syringe and the channel 140. In the third embodiment, the syringe immediately pushes the elastic material of the proximal face 182 over the spike to open the slit 181 whereupon further inward movement pushes the slit past the side openings 149 to seal and establish fluid flow path between the syringe and the channel 140.

The stopper is made from an elastic, preferably elastomeric material such as silicone, so that once a fluid transfer device is removed from the female Luer body, the proximal face 182 will resiliently move proximally to its original closed position. When not in use, the proximal face 182 of the stopper 160 is preferably flush with proximal wall 112 of the female Luer body 100, so that both the proximal wall 112 and the proximal face 182 can be swabbed with a disinfectant. In one embodiment, the proximal face 182 is fully closed when the stopper 160 is not in use, and has a reversibly openable slit 181 in a central portion of the face 182. In this case the walls of the slit 181 preferably contact one another when the elastic material of the stopper 160 is relaxed (i.e. when the stopper 160 is not in use) in order to close the opening in the proximal end 162 of the stopper 160 and prevent contamination of the present device. The walls of the slit 181 can be urged open when a syringe or other fluid conduit presses against the proximal face 182 of the stopper 160.

Additional slits 181 can be included in the face 182, for example two slits intersecting to form an "x" can be used.

In order to better retain the elastic stopper 160 within the female Luer body 100, the stopper 160 is provided with a retaining groove 184 having an inwardly extending annular wall 185, preferably at the distal end 164 of the stopper 160. The retaining groove 184 surrounds the annular flange 141 of the channel insert 150 (see FIG. 20) such that a distally facing, outwardly extending distal wall 141a is engaged by a proximally facing, inwardly extending surface 185 of the retaining groove 184 and restrains the lateral, and in particular proximal, movement of the stopper 160. In addition, the exterior 165 of the stopper 160 is preferably provided with an outwardly extending, annular projection 186 having a proximal face 187 which is adapted to engage the inwardly extending wall 114 of the interior 101 of the female Luer body 100 (see FIG. 20.) This further restrains the proximal movement of the stopper 160.

The female Luer body 100 and channel insert 150 are placed in fluid communication with the male Luer member 20 of the male Luer body 10 via a seal 170 (see FIGS. 28-32), which is preferably formed from an elastomeric or other elastic material such as silicone. The seal 170 preferably has a generally cylindrical shape with a fluid flow passageway 171 extending from an off-center positioned proximal end 172 to an axially aligned distal end 174. The off-center opening 179 in the proximal face 178 aligns the fluid flow channel 171 with the channel distal opening 143 of the channel insert 150 in order to allow a flow of fluid through the connector assembly 1.

The seal 170 is preferably partially compressed between the distal surface 151 of the channel insert 150 and the wall at the distal end 44 of the male Luer body 10. The seal 170 has at least one axially extending groove 173 on its annular surface which mates with at least one axially extending seal peg 41 in the male Luer body 40 in order to prevent rotation of the seal 170. In addition, an axially extending, annular flange or ring 175 is provided on the distal face 176 of the seal 170. The flange 175 fits within the groove 49 in the receptacle 40 of the male Luer body 10 in the manner of an O-ring, in order to maintain a seal at higher pressures. The flange 175 also allows the seal 170 to maintain a seal when fluid flow in either direction through the present connector assembly 1, and also helps to prevent fluid from passing around the seal 170 rather than through the flow passageway 171.

Connector Assembly

To assemble the present connector assembly 1, the stopper 160 is placed around the channel insert 150, and this subassembly is placed through the distal end 104 of the female Luer body 100 to form a female Luer subassembly. The seal 170 is then placed in the distal end 44 of the receptacle 40 of the male Luer body 10 such that the flange 175 is seated within the groove 49 in the receptacle 40 and the seal pegs 41 are retained by the grooves 173, thereby forming a male Luer subassembly. The female Luer subassembly can then be joined to the male Luer subassembly by placing the distal end 104 of the female Luer body 100 within the proximal end 12 of the male Luer body 10 such that the cam post 110 on the female Luer body 100 is placed within the cam groove 50 of the male Luer body 10. The female Luer body 100 can then be rotated in order to secure the subassemblies to one another.

Except as described otherwise herein with respect to the stopper 160 and seal 170, the components of the connector assembly 1 can be made of any suitably rigid material used for medical applications, such as polycarbonate or other medical grade plastic.

In the first embodiment, the outer surface 121 of the flange 120 of the female Luer body 100 included the embossed word "Close." At rest with the valve 1 closed, the word "Close" is not be covered by the semi-annular shield 60, thereby visually indicating that the valve 1 was in its closed position. Upon being engaged by an access device to twist the valve 1 open, the shield 60 rotates over and therefore conceals the word "Close," thereby visually indicating that the valve was in its open position.

In lieu of the visual indication of the first embodiment, as shown in FIGS. 33 B & C, in the second and third embodiments, there is provided a bold triangular first indicator 200, preferably colored "green" that is formed on the lateral side 18 of the male Luer body 10. A second bold triangular indicator 202, preferably colored "green" is formed on the outer surface 121 of flange 120 of the channel insert 150. The indicators 200 and 202 are diametrically opposed when the valve 1 is in its closed position and are aligned when the valve 1 is in its open position due to the 180 degree path of the cam groove 50, thereby visually indicating the open or closed state of the valve 1. Moreover, unlike the first embodiment, the indicators 200 and 202 that precisely align when the valve 1 is open, clearly indicating when the valve 1 is fully open.

In a variation to the second and third embodiments, a pair of diametrically-opposed green-colored indicators 200 and 202 are formed on the lateral side 18 and outer surface 121. Another pair of indicators 204, preferably colored "red" are formed on the lateral side 18 of the male Luer body 10 at a smaller angular distance (e.g., 120 degrees). The cam groove 50 is formed at the same angular distance to define a lesser angular path (e.g., 120 degrees). When the valve 1 is closed, the green indicators 202 on the outer surface 121 of flange 120 are aligned with the red indicators 104 on the lateral side 18 of the male Luer body 10, thereby visually indicating that the valve 1 is closed. However, when the valve 1 is open, the green indicators 202 on the outer surface 121 of flange 120 are aligned with the green indicators 200 on the lateral side 18 of the male Luer body 10, thereby visually indicating that the valve 1 is open. It is noted that having the indicators 200, 202 and 204 positioned at 120 degrees increases the visibility at all angles and due to their precise alignments, precisely visually indicate when the valve 1 is fully open or fully closed.

Although the present invention has been described in considerable detail with reference to certain preferred embodiments, other embodiments are possible. Therefore, the scope of the appended claims should not be limited to the description of preferred embodiments contained in this disclosure. Recitation of value ranges herein is merely intended to serve as a shorthand method for referring individually to each separate value falling within the range. Unless otherwise indicated herein, each individual value is incorporated into the specification as if it were individually recited herein. All references cited herein are incorporated by reference in their entirety.

What is claimed is:

1. A medical connector assembly having a longitudinal axis, the medical connector assembly comprising:
   a male luer body having a proximal end, a distal end, and a flow channel extending between said proximal end and said distal end, said distal end comprising a tapered male luer member having an open end adapted to be connected to a fluid conduit;
   a female luer assembly, comprising: a female luer body having a proximal end, a distal end, and a flow channel extending between said proximal end of said female luer body and said distal end of said female luer body, said proximal end of said female luer body forming a female luer member for receiving a male luer member of a fluid transfer device; said female luer body comprising a cam post;
   a fluid channel insert having a proximal end, a distal end, and an inner surface defining a flow channel extending between said proximal end of said fluid channel insert and said distal end of said fluid channel insert, wherein said flow channel of said fluid channel insert is offset from said longitudinal axis at said distal end of said fluid channel insert, said fluid channel insert further comprising an annular medial wall at said distal end of said fluid channel insert, said annular medial wall engaging said distal end of said female luer body; said proximal end of the fluid channel insert comprising a tubular conduit having an opening at a proximal end of said tubular conduit; said fluid channel insert further comprises an annular barb shaped flange extending outwardly from said tubular conduit between an outwardly extending medial wall and said proximal end of said fluid channel insert;
   an elastomeric seal having a proximal end, a distal end, and a flow channel extending between said proximal end of said elastomeric seal and said distal end of said elastomeric seal, wherein said flow channel of said elastomeric seal is offset from said longitudinal axis at said proximal end of said elastomeric seal and is adapted to provide fluid communication with said flow channel of said fluid channel insert at said distal end of said fluid channel insert; and
   an elastomeric stopper having a proximal end and a distal end, said elastomeric stopper having a flush surface at said proximal end of said elastomeric stopper, said flush surface comprising a slit to allow an opening to be formed by deforming said proximal end of said elastomeric stopper, said elastomeric stopper further comprising an annular groove adapted to mate with said annular barb shaped flange of said fluid channel insert; and
   wherein said distal end of said female luer body is received in a receptacle in the male luer body to connect with said proximal end of said male luer body with an interference fit and forms a flow channel through said medical connector assembly when said flow channel of said male luer body and said flow channel of said female luer body are aligned;
   wherein the proximal end of said male luer body further comprises a cam groove and first and second protrusions; said first and second protrusions extending into the cam groove at respective first and second lateral ends of the cam groove; said cam groove extending around a portion of a circumference of the proximal end of the male luer body surrounding the receptacle, said cam groove being shaped to receive said cam post of the female luer body and to define a range of rotation of the female luer body with respect to the male luer body, with the cam post configured to snap over the first protrusion at the first lateral end of the cam groove, and to snap over the second protrusion at the second lateral end of the cam groove.

2. The medical connector assembly of claim 1, further comprising a cap, said cap having an open proximal end, a closed distal end, and a longitudinal axis-between said open proximal end of said cap and said closed distal end of said cap, said open proximal end of said cap being sized to fit on said tapered male luer member of said male luer body.

3. The medical connector assembly as set forth in claim 1, wherein an exterior surface of said elastomeric stopper and an interior surface of said female luer body comprise interlocking walls precluding removal of said elastomeric stopper from said female luer body.

4. The medical connector assembly as set forth in claim 1, where said proximal end of said fluid channel insert comprises at least one longitudinal groove in the inner surface for grasping said proximal end of said elastomeric stopper when elastic material of said proximal end of said elastomeric stopper is urged into the at least one longitudinal groove from within the flow channel, thereby hindering relative rotational movement between said fluid channel insert and said elastomeric stopper when the medical connector assembly is accessed by said male luer member of said fluid transfer device.

5. The medical connector assembly as set forth in claim 4, wherein the at least one longitudinal grove comprises a plurality of grooves oriented frustroconically.

6. The medical connector assembly as set forth in claim 1, wherein said distal end of said female luer body and said distal end of said fluid channel insert comprise interlocking grooves and projections precluding relative rotation between said female luer body and said fluid channel insert.

7. The medical connector assembly as set forth in claim 6, wherein said interlocking grooves are formed on an outside surface of said fluid channel insert and said projections are formed on an inside surface of said female luer body.

8. The medical connector assembly as set forth in claim 6, wherein said interlocking grooves and said projections are oriented frustroconically.

9. The medical connector assembly as set forth in claim 1, wherein said cam post of said female luer body and said cam groove of said male luer body comprise an interlocking cam groove and an interlocking cam post that preclude over-rotation of said female luer body relative to said male luer body.

10. A medical connector assembly having a longitudinal axis, the medical connector assembly comprising:

a male luer body having a proximal end, a distal end, and a flow channel extending between said proximal end and said distal end, said distal end comprising a tapered male luer member having an open end adapted to be connected to a fluid conduit;

a female luer body having a proximal end, a distal end, and a flow channel extending between said proximal end of said female luer body and said distal end of said female luer body, said proximal end of said female luer body forming a female luer member for receiving a male luer member of a fluid transfer device; said female luer body comprising a cam post;

a fluid channel insert having a proximal end, a distal end, a flow channel extending between said proximal end of said fluid channel insert and said distal end of said fluid channel insert, and an annular medial wall at said distal end of said fluid channel insert, said annular medial wall engaging said distal end of said female luer body; said proximal end of the fluid channel insert comprising a tubular conduit having an opening at a proximal end of said tubular conduit;

an elastomeric seal having a proximal end, a distal end, and a flow channel extending between said proximal end of said elastomeric seal and said distal end of said elastomeric seal, wherein said flow channel of said elastomeric seal is adapted to provide fluid communication with said flow channel of said fluid channel insert at said distal end of said fluid channel insert; and an elastomeric stopper having a proximal end and a distal end, said elastomeric stopper having a flush surface at said proximal end of said elastomeric stopper, said flush surface comprising a slit to allow an opening to be formed by deforming said proximal end of said elastomeric stopper; and wherein said distal end of said female luer body is received in a receptacle in the male luer body to connect with said proximal end of said male luer body with an interference fit and forms a flow channel through said medical connector assembly when said flow channel of said male luer body and said flow channel of said female luer body are aligned;

wherein the proximal end of said male luer body further comprises a cam groove and first and second protrusions; said first and second protrusions extending into the cam groove at respective first and second lateral ends of the cam groove; said cam groove extending around a portion of a circumference of the proximal end of the male luer body surrounding the receptacle, said cam groove being shaped to receive said cam post of the female luer body and to define a range of rotation of the female luer body with respect to the male luer body, with the cam post configured to snap over the first protrusion at the first lateral end of the cam groove, and to snap over the second protrusion at the second lateral end of the cam groove.

11. The medical connector assembly as set forth in claim 10, further comprising a cap, said cap having an open proximal end, a closed distal end, and a longitudinal axis-between said open proximal end of said cap and said closed distal end of said cap, said open proximal end of said cap being sized to fit on said tapered male luer member of said male luer body.

12. The medical connector assembly as set forth in claim 10, wherein an exterior surface of said elastomeric stopper and an interior surface of said female luer body comprise interlocking walls precluding removal of said elastomeric stopper from said female luer body.

13. The medical connector assembly as set forth in claim 10, wherein said distal end of said female luer body and said distal end of said fluid channel insert comprise interlocking grooves and projections precluding relative rotation between said female luer body and said fluid channel insert.

14. The medical connector assembly as set forth in claim 13, wherein said interlocking grooves are formed on an outside surface of said fluid channel insert and said projections are formed on an inside surface of said female luer body.

15. The medical connector assembly as set forth in claim 10, wherein said cam post of said female luer body and said cam groove of said male luer body comprise an interlocking cam groove and an interlocking cam post that preclude over-rotation of said female luer body relative to said male luer body.

16. A medical connector assembly having a longitudinal axis, the medical connector assembly comprising:

a male luer body having a proximal end, a distal end, and a flow channel extending between said proximal end and said distal end, said distal end comprising a tapered male luer member having an open end adapted to be connected to a fluid conduit;

a female luer body having a proximal end, a distal end, and a flow channel extending between said proximal end of said female luer body and said distal end of said female luer body, said proximal end of said female luer body forming a female luer member for receiving a male luer member of a fluid transfer device;

a fluid channel insert having a proximal end, a distal end, an inner surface defining a flow channel extending between said proximal end of said fluid channel insert and said distal end of said fluid channel insert, and an annular medial wall at said distal end of said fluid channel insert, said annular medial wall engaging said distal end of said female luer body; said proximal end of the fluid channel insert comprising a tubular conduit having an opening at a proximal end of said tubular conduit;

an elastomeric seal having a proximal end, a distal end, and a flow channel extending between said proximal end of said elastomeric seal and said distal end of said elastomeric seal, wherein said flow channel of said elastomeric seal is adapted to provide fluid communication with said flow channel of said fluid channel insert at said distal end of said fluid channel insert; and an elastomeric stopper having a proximal end and a distal end, said elastomeric stopper having a flush surface at said proximal end of said elastomeric stopper, said flush surface comprising a slit to allow an opening to be formed by deforming said proximal end of said elastomeric stopper; and wherein said distal end of said female luer body connects with said proximal end of said male luer body with an interference fit and forms a flow channel through said medical connector assembly when said flow channel of said male luer body and said flow channel of said female luer body are aligned;

where said proximal end of said fluid channel insert comprises at least one longitudinal groove in the inner surface for grasping said proximal end of said elastomeric stopper when elastic material of said proximal end of said elastomeric stopper is urged into the at least one longitudinal groove from within the flow channel of said fluid channel insert, thereby hindering relative rotational movement between said fluid channel insert and said elastomeric stopper when the medical connector assembly is accessed by said male luer member of said fluid transfer device.

17. The medical connector assembly as set forth in claim 16, wherein the at least one longitudinal grove comprises a plurality of grooves oriented frustroconically.

18. The medical connector assembly as set forth in claim 16, wherein said distal end of said female luer body and said distal end of said fluid channel insert comprise interlocking grooves and projections precluding relative rotation between said female luer body and said fluid channel insert.

19. The medical connector assembly as set forth in claim 18, wherein said interlocking grooves are formed on an outside surface of said fluid channel insert and said projections are formed on an inside surface of said female luer body.

20. The medical connector assembly as set forth in claim 18, wherein said interlocking grooves and said projections are oriented frustroconically.

* * * * *